United States Patent
Sarafianos et al.

(10) Patent No.: US 10,759,774 B2
(45) Date of Patent: Sep. 1, 2020

(54) INHIBITORS OF HEPATITIS B VIRUS TARGETING CAPSID ASSEMBLY

(71) Applicants: THE CURATORS OF THE UNIVERSITY OF MISSOURI, Columbia, MO (US); REGENTS OF THE UNIVERSITY OF MINNESOTA, Minneapolis, MN (US)

(72) Inventors: Stefan G. Sarafianos, Columbia, MO (US); Zhengqiang Wang, Eden Prairie, MO (US); Andrew D. Huber, Columbia, MO (US); Jing Tang, Shoreview, MN (US)

(73) Assignees: THE CURATORS OF THE UNIVERSITY OF MISSOURI, Columbia, MO (US); REGENTS OF THE UNIVERSITY OF MINNESOTA, Minneapolis, MN (US)

(*) Notice: Subject to any disclaimer, the term of this patent is extended or adjusted under 35 U.S.C. 154(b) by 0 days.

(21) Appl. No.: 16/144,274

(22) Filed: Sep. 27, 2018

(65) Prior Publication Data

US 2019/0092742 A1  Mar. 28, 2019

Related U.S. Application Data

(60) Provisional application No. 62/564,865, filed on Sep. 28, 2017.

(51) Int. Cl.
| | | |
|---|---|---|
| *C07D 333/38* | (2006.01) | |
| *A61K 31/381* | (2006.01) | |
| *A61P 31/20* | (2006.01) | |
| *C07D 409/12* | (2006.01) | |
| *C07D 417/12* | (2006.01) | |
| *C07D 495/04* | (2006.01) | |
| *A61K 31/506* | (2006.01) | |
| *A61K 31/18* | (2006.01) | |
| *A61K 31/5377* | (2006.01) | |
| *A61K 31/4155* | (2006.01) | |
| *A61K 31/427* | (2006.01) | |
| *A61K 31/519* | (2006.01) | |
| *A61K 31/4365* | (2006.01) | |

(52) U.S. Cl.
CPC ............ *C07D 333/38* (2013.01); *A61K 31/18* (2013.01); *A61K 31/381* (2013.01); *A61K 31/4155* (2013.01); *A61K 31/427* (2013.01); *A61K 31/4365* (2013.01); *A61K 31/506* (2013.01); *A61K 31/519* (2013.01); *A61K 31/5377* (2013.01); *A61P 31/20* (2018.01); *C07D 409/12* (2013.01); *C07D 417/12* (2013.01); *C07D 495/04* (2013.01)

(58) Field of Classification Search
CPC .. C07D 333/38; C07D 409/12; C07D 417/12; C07D 495/04; A61K 31/427; A61K 31/4365; A61K 31/519; A61K 31/4155; A61K 31/5377; A61K 31/18; A61K 31/506; A61K 31/381; A61P 31/20
See application file for complete search history.

(56) References Cited

FOREIGN PATENT DOCUMENTS

DE  19817264 A1  10/1999

OTHER PUBLICATIONS

Sergiy M. Kovalenko, Sergiy V. Vlasov, and Valentin P. Chernykh, Synthesis of 5-Methyl-4-oxo-2-(coumarin-3-yl)-N-aryl-3,4-dihydrothieno[2,3-d]-pyrimidine-6-carboxamides, Heteroatom Chemistry vol. 18, No. 4, 2007, 341-346 (Year: 2007).*
Bourne, et al., "Small-Molecule Effectors of Hepatitis B Virus Capsid Assembly Give Insight into Virus Life Cycle," Journal of Virology 82(20):10262-10270 (2008).
Cai, et al., "Identification of Disubstituted Sulfonamide Compounds as Specific Inhibitors of Hepatitis B Virus Covalently Closed Circular DNA Formation," Antimicrobial Agents and Chemotherapy 56(8):4277-4288 (2012).
Campagna, et al., "Sulfamoylbenzamide Derivatives Inhibit the Assembly of Hepatitis B Virus Nucleocapsids," Journal of Virology 87(12):6931-6942 (2013).
Cox and Tillman, "Emerging Pipeline Drugs for Hepatitis B Infection," Expert Opinion on Emerging Drugs 16(4):713-729 (2011).
Delaney, IV, et al., "Phenylpropenamide Derivatives AT-61 and AT-130 Inhibit Replication of Wild-Type and Lamivudine-Resistant Strains of Hepatitis B Virus in Vitro," Antimicrobial Agents and Chemotherapy 46(9):3057-3060 (2002).
Deres, et al., "Inhibition of Hepatitis B Virus Replication by Drug-Induced Depletion of Nucleocapsids," Science 299(5608):893-896 (2003).
Feld, et al., "The Phenylpropenamide Derivative AT-130 Blocks HBV Replication at the Level of Viral RNA Packaging," Antiviral Research 76(2):168-177 (2007).
Huber, et al., 3-Hydroxypyrimidine-2,4-Diones as Novel Hepatitis B Virus Antivirals Targeting the Viral Ribonuclease H, Antimicrobial Agents and Chemotherapy 61(6):e00245-17 (2017).
Klumpp, et al., "High-Resolution Crystal Structure of a Hepatitis B Virus Replication Inhibitor Bound to the Viral Core Protein," Proceedings of the National Academy of Sciences of the United States of America 112(49):15196-15201 (2015).
Perni, et al., "Phenylpropenamide Derivatives as Inhibitors of Hepatitis B Virus Replication," Bioorganic & Medicinal Chemistry Letters 10(23):2687-2690 (2000).
Qui, et al., "Design and Synthesis of Orally Bioavailable 4-Methyl Heteroaryldihydropyrimidine Based Hepatitis B Virus (HBV) Capsid Inhibitors," Journal of Medicinal Chemistry 59(16):7651-7666 (2016).
Stray, et al., "A Heteroaryldihydropyrimidine Activates and Can Misdirect Hepatitis B Virus Capsid Assembly," Procedures of the National Academy of Sciences of the United States of America 102(23):8138-8143 (2005).

(Continued)

*Primary Examiner* — Sarah Pihonak
*Assistant Examiner* — Jason Deck
(74) *Attorney, Agent, or Firm* — Dentons US LLP

(57) ABSTRACT

The present invention provides novel compounds and methods for treating, preventing or inhibiting hepatitis B virus (HBV).

6 Claims, 10 Drawing Sheets
Specification includes a Sequence Listing.

(56) References Cited

OTHER PUBLICATIONS

Stray and Zlotnick, "BAY 41-4109 Has Multiple Effects on Hepatitis B Virus Capsid Assembly," Journal of Molecular Recognition 19(6):542-548 (2006).

Venkatakrishnan, et al., "Hepatitis B Virus Capsids Have Diverse Structural Responses to Small-Molecule Ligands Bound to the Heteroaryldihydropyrimidine Pocket," Journal of Virology 90(8):3994-4004 (2016).

Weber, et al., "Inhibition of Human Hepatitis B Virus (HBV) by a Novel Non-Nucleosidic Compound in a Transgenic Mouse Model," Antiviral Research 54(2):69-78 (2002).

Wu, et al., "Preclinical Characterization of GLS4, an Inhibitor of Hepatitis B Virus Core Particle Assembly," Antimicrobial Agents and Chemotherapy 57(11):5344-5354 (2013).

Zhou, et al., "Heteroaryldihydropyrimidine (HAP) and Sulfamoylbenzamide (SBA) Inhibit Hepatitis B Virus Replication by Different Molecular Mechanisms," Science Reports 7:42374 (2017).

Zlotnick, et al., "A Small Molecule Inhibits and Misdirects Assembly of Hepatitis B Virus Capsids," Journal of Virology 76(10):4848-4854 (2002).

\* cited by examiner

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
cctggttatc gctggatgtg t        21

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2

```
ggacaaacgg gcaacatacc tt                                              22

<210> SEQ ID NO 3
<211> LENGTH: 29
<212> TYPE: DNA
<213> ORGANISM: Artificial Sequence
<220> FEATURE:
<223> OTHER INFORMATION: Primer

<400> SEQUENCE: 3
ggcctttctg tgtaaacaat acctgaacc                                       29

<210> SEQ ID NO 4
<211> LENGTH: 30
<212> TYPE: DNA
<213> ORGANISM: Artificial Sequence
<220> FEATURE:
<223> OTHER INFORMATION: Primer

<400> SEQUENCE: 4
gtaatcgagc tccggtggtc tccatgcgac                                      30
```

INHIBITORS OF HEPATITIS B VIRUS TARGETING CAPSID ASSEMBLY

CROSS REFERENCE TO RELATED APPLICATIONS

This application claims the benefit of U.S. Provisional Application 62/564,865, filed Sep. 28, 2017, which is incorporated herein by reference in its entirety.

STATEMENT OF GOVERNMENT SUPPORT

The invention was made with government support under contract No. R01-AI121315 awarded by the National Institutes of Health/National Institute of Allergy and Infectious Diseases. The government has certain rights in the invention.

INCORPORATION OF SEQUENCE LISTING

The sequence listing that is contained in the file named "UVMO118US_ST25.txt", which is 1 kilobyte as measured in Microsoft Windows operating system and was created on Sep. 27, 2018, is filed electronically herewith and incorporated herein by reference.

FIELD OF THE INVENTION

The present invention relates to the field of antiviral medicine and antiviral therapy, and more specifically to methods of and inhibitors for preventing, treating, or reducing the spread of hepatitis B virus (HBV) infections.

BACKGROUND OF THE INVENTION

Hepatitis B virus (HBV) is a small, enveloped DNA virus of the Hepadnaviridae family that has highly specific tropism for liver cells. Chronic infection leads to liver disease, hepatocellular carcinoma (HCC), liver cirrhosis, and other complications. Globally, almost 50% of all HCC cases are linked to chronic HBV infection. Currently, an estimated 240 million worldwide are chronically infected, and there are approximately 0.5-1 million deaths per year due to HBV-related liver conditions.

HBV has a partially double-stranded circular DNA genome, relaxed circular DNA (rcDNA), that is completed by host enzymes in the nuclei of newly infected cells to covalently closed circular DNA (cccDNA). The cccDNA is the template for viral transcripts, including a full-length pre-genomic RNA (pgRNA) that is packaged and reverse transcribed to rcDNA by the viral polymerase. The rcDNA can either enter the nucleus to amplify the cccDNA pool, or it can exit the cell in a mature virion.

Currently, HBV treatment options include only nucleoside reverse transcriptase inhibitors (NRTIs) and the immunomodulatory agent interferon alpha (IFN-α). NRTIs are able to clear the virus to undetectable levels; however, after cessation of therapy, patients' viral loads often rebound. This rebound is likely due to failure of NRTIs to clear the HBV cccDNA present in hepatocytes, and viral components are produced from the residual cccDNA, which can persist for decades. NRTI regimens, therefore, must be long-term, most likely lifelong. IFN-α treatment, on the other hand, is able to clear cccDNA, but virological response is only observed in <10% of patients. IFN-α treatment also leads to adverse side effects that often outweigh the potential benefits of treatment. New treatments, therefore, are highly desired for HBV therapy.

SUMMARY OF INVENTION

The present disclosure provides a composition comprising a compound of formula (I):

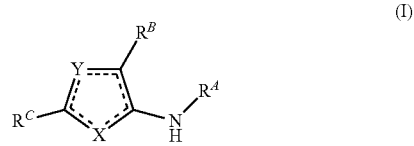

(I)

wherein X or Y is a heteroatom such as S, O, NH, or a substituted methine group; RA is a H, acyl or sulfonyl group as shown by:

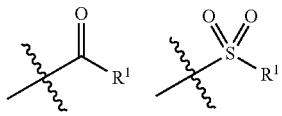

wherein R1 is an alkyl, cycloalkyl or substituted aryl group; wherein RB is a cyano, ester, carboxamide, thiocarboxamide or a substituted carboxamide as shown by:

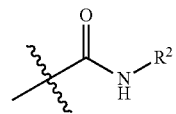

wherein R2 is an alkyl, cycloalkyl or substituted aryl group; alternatively, RA and RB form a six-membered heterocyclic ring as shown by:

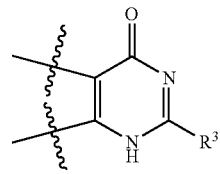

wherein R3 is an alkyl, cycloalkyl or substituted aryl group; and wherein RC is a carboxamide as shown by:

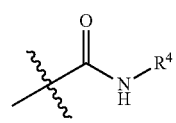

wherein R4 is an alkyl, cycloalkyl or substituted aryl group; or a sulfonamide as shown by:

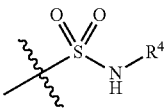

wherein $R^4$ is an alkyl, cycloalkyl or substituted aryl group.

In certain embodiments, the composition comprises a compound of formula (II):

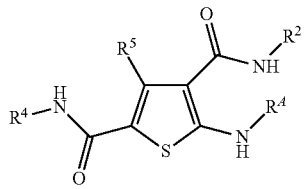

(II)

wherein $R^2$ is an alkyl, cycloalkyl or substituted aryl group; $R^4$ is an alkyl, cycloalkyl or substituted aryl group; and $R^5$ is an alkyl or cycloalkyl group.

In other embodiments, the composition comprises a compound of formula (III):

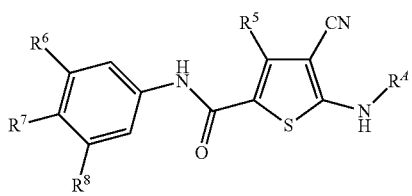

(III)

wherein $R^5$ is an alkyl or cycloalkyl group; $R^6$, $R^7$, and $R^8$ are independently a H, alkyl, alkoxy, $CF_3$, $CHF_2$, $CH_2F$, halogen (F, Cl, Br, I), CN, hydroxyl, amino, carboxamide, sulfonamide, sulfonyl, or carboxylic acid.

In further embodiments, the composition comprises a compound of formula (IV):

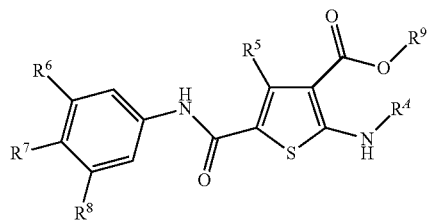

(IV)

wherein R5 is an alkyl or cycloalkyl group; R6, R7, and R8 are independently a H, alkyl, alkoxy, CF3, CHF2, CH2F, halogen (F, Cl, Br, I), CN, hydroxyl, amino, carboxamide, sulfonamide, sulfonyl, carboxylic acid; R9 is H, alkyl, cycloalkyl, or substituted aryl group.

In additional embodiments, the composition comprises a compound of formula (V):

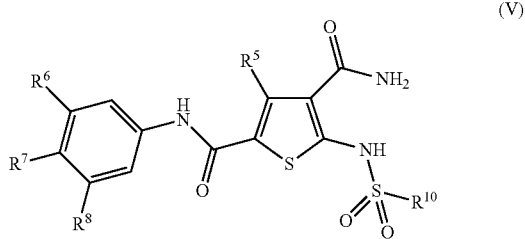

(V)

wherein $R^5$ is an alkyl or cycloalkyl group; $R^6$, $R^7$, and $R^8$ are independently a H, alkyl, alkoxy, $CF_3$, $CHF_2$, $CH_2F$, halogen (F, Cl, Br, I), CN, hydroxyl, amino, carboxamide, sulfonamide, sulfonyl, or carboxylic acid; and $R^{10}$ is an alkyl, cycloalkyl, or substituted aryl group.

In some embodiments, the composition comprises a compound of formula (VI):

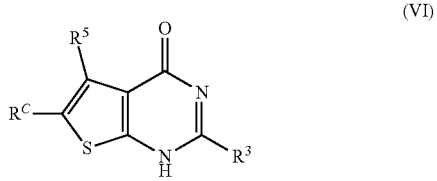

(VI)

wherein $R^5$ is an alkyl or cycloalkyl group; and $R^3$ is an alkyl, cycloalkyl or substituted aryl group.

In yet other embodiments, the composition comprises a compound of formula (VII):

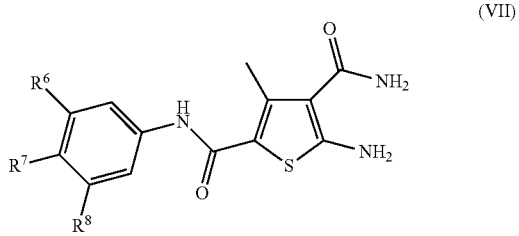

(VII)

wherein $R^5$, $R^6$, and $R^7$ are independently a H, alkyl, alkoxy, $CF_3$, $CHF_2$, $CH_2F$, halogen (F, Cl, Br, I), CN, hydroxyl, amino, carboxamide, sulfonamide, sulfonyl, or a carboxylic acid.

In certain embodiments, the compound is ZW-769, ZW-770, ZW-771, ZW-772, ZW-773, ZW-774, ZW-775, ZW-776, ZW-777, ZW-790, ZW 791, ZW-792, ZW 793, ZW-794, ZW-892, ZW-893, ZW-894, ZW-895, ZW 896, ZW-932, ZW-933, ZW 934, ZW-935, ZW 936, ZW-937, ZW-938, ZW-939, ZW 1034, ZW-1035, ZW-1036, ZW-1037, ZW-1038, ZW-1039, ZW-1040, ZW-1041, ZW 1042, ZW-1043, ZW-1044, ZW 1045, ZW-1046, ZW 1047, ZW-1048, ZW-1049, ZW 1050, ZW-1051, ZW-1052, ZW 1053, ZW-1054, ZW 1055, ZW-1056, ZW-1057, ZW 1066, ZW-1067, ZW-1068, ZW 1069, ZW-1070, ZW 1071, ZW-1072, ZW-1073, or ZW-1074, the chemical structures of which are shown in Table 2. In particular embodiments, the compound is ZW-769, ZW-770, ZW-790, ZW 791, ZW-794, ZW-892, ZW-893, ZW-894, ZW-896, ZW-932, ZW-933, ZW-934, ZW 935, ZW-1034, ZW-1037, ZW-1039, ZW-1040, ZW-1042, ZW-1043, ZW-1044, ZW 1045, ZW-1046, ZW-1048, ZW 1050, ZW 1051, ZW-1052, ZW 1053, ZW-1054, ZW 1055, ZW-1056, ZW-1057, ZW 1066, ZW 1067, ZW-1068, ZW 1069, or ZW-1073.

In additional embodiments, the composition comprises a plurality of compounds of formula (I). In further embodiments, the compound has antiviral properties. In other embodiments, the composition further comprises an additional antiviral compound. In particular embodiments, the additional antiviral compound is a heteroaryldyhydropyrimidine (HAP) or a sulfamoylbenzamide (SBA). In yet other embodiments, the composition further comprises a pharmaceutically acceptable excipient.

The present disclosure thus provides a pharmaceutical composition comprising a composition as disclosed herein above, and a pharmaceutically acceptable excipient. In some embodiments, the compound is ZW-769, ZW-770, ZW-771, ZW-772, ZW-773, ZW-774, ZW-775, ZW-776, ZW-777, ZW-790, ZW 791, ZW-792, ZW-793, ZW-794, ZW-892, ZW-893, ZW 894, ZW-895, ZW 896, ZW 932, ZW 933, ZW-934, ZW 935, ZW 936, ZW-937, ZW 938, ZW-939, ZW-1034, ZW 1035, ZW-1036, ZW-1037, ZW-1038, ZW-1039, ZW 1040, ZW-1041, ZW-1042, ZW 1043, ZW 1044, ZW-1045, ZW 1046, ZW 1047, ZW-1048, ZW-1049, ZW-1050, ZW 1051, ZW 1052, ZW-1053, ZW 1054, ZW 1055, ZW-1056, ZW-1057, ZW-1066, ZW 1067, ZW 1068, ZW-1069, ZW 1070, ZW 1071, ZW-1072, ZW-1073, or ZW-1074, the chemical structures of which are shown in Table 2. In other embodiments, the compound is ZW-769, ZW-770, ZW-790, ZW 791, ZW-794, ZW-892, ZW-893, ZW-894, ZW-896, ZW-932, ZW 933, ZW-934, ZW-935, ZW 1034, ZW-1037, ZW-1039, ZW-1040, ZW-1042, ZW 1043, ZW-1044, ZW-1045, ZW 1046, ZW-1048, ZW 1050, ZW 1051, ZW-1052, ZW 1053, ZW-1054, ZW 1055, ZW 1056, ZW-1057, ZW 1066, ZW 1067, ZW-1068, ZW 1069, or ZW-1073.

In further embodiments, the pharmaceutical composition comprises a plurality of the presently disclosed compounds. In certain embodiments, the compound has antiviral properties. In additional embodiments, the pharmaceutical composition further comprises an additional antiviral compound, such as a heteroaryldyhydropyrimidine (HAP) or a sulfamoylbenzamide (SBA).

Additionally, the present disclosure provides a method of inhibiting the replication of a hepatitis B virus (HBV) comprising contacting said HBV with at least a first compound as disclosed herein. In certain embodiments, the HBV is present inside of a cell, and the contacting comprises contacting the cell with the compound. In particular embodiments, the is present in a mammal, for example a human subject. In some embodiments, the at least a first compound HF9C6 is ZW-769, ZW-770, ZW-790, ZW 791, ZW-794, ZW-892, ZW-893, ZW-894, ZW-896, ZW 932, ZW-933, ZW-934, ZW-935, ZW 1034, ZW-1037, ZW-1039, ZW-1040, ZW-1042, ZW-1043, ZW-1044, ZW-1045, ZW 1046, ZW-1048, ZW 1050, ZW-1051, ZW-1052, ZW 1053, ZW-1054, ZW 1055, ZW 1056, ZW-1057, ZW 1066, ZW-1067, ZW-1068, ZW 1069, or ZW-1073. In other embodiments, the at least a first composition comprises a plurality of compounds as disclosed herein. In further embodiments, the composition further comprises an additional antiviral compound. Such additional antiviral compounds include, but are not limited to, a heteroaryldyhydropyrimidine (HAP) or a sulfamoylbenzamide (SBA). In yet other embodiments, the composition further comprises a pharmaceutically acceptable excipient.

The present disclosure also provides a method of treating a mammal having a HBV infection, comprising administering to said mammal a composition comprising at least a first compound as disclosed herein and a pharmaceutically acceptable excipient. In certain embodiments, the at least a first compound is ZW-769, ZW-770, ZW-790, ZW 791, ZW-794, ZW-892, ZW-893, ZW-894, ZW-896, ZW 932, ZW-933, ZW 934, ZW-935, ZW 1034, ZW-1037, ZW-1039, ZW-1040, ZW-1042, ZW-1043, ZW 1044, ZW-1045, ZW 1046, ZW-1048, ZW 1050, ZW 1051, ZW-1052, ZW 1053, ZW 1054, ZW 1055, ZW 1056, ZW-1057, ZW 1066, ZW 1067, ZW-1068, ZW 1069, or ZW-1073. In other embodiments, the at least a first composition comprises a plurality of compounds as disclosed herein. In further embodiments, the composition further comprises an additional antiviral compound, such as a heteroaryldyhydropyrimidine (HAP) or a sulfamoylbenzamide (SBA). In yet other embodiments, the composition further comprises a pharmaceutically acceptable excipient. In some embodiments, the mammal is a human subject.

The present disclosure further provides a method of curing a mammal having a HBV infection, comprising administering to said mammal a pharmaceutical composition comprising at least a first compound as disclosed herein and a pharmaceutically acceptable excipient. In certain embodiments, the mammal is a human subject.

The present disclosure additionally provides a method of preventing an HBV infection in a mammal, comprising administering to said mammal before said HBV infection a pharmaceutical composition comprising at least a first compound as disclosed herein and a pharmaceutically acceptable excipient. In particular embodiments, the mammal is a human subject.

BRIEF DESCRIPTION OF THE DRAWINGS

FIG. 1A. Schematic of thermal shift assay (TSA). FIG. 1B. TSA was performed under non-assembly (solid line) and full assembly (dotted line) conditions for Cp. FIG. 1C. TSA was performed for Cp in the presence or absence of Bay 38-7690 under the final optimized reaction conditions described in the Examples section, below. FIG. 1D. Cp thermal shift profile for hit compound HF4H3. FIG. 1E. Cp thermal shift profile for hit compound HF4E6. FIG. 1F. Cp thermal shift profile for hit compound HF9C6. FIG. 1G. Cp thermal shift profile for hit compound HF12E9. FIG. 1H. Cp thermal shift profile for hit compound HF15B9. FIG. 1I. Cp thermal shift profile for hit compound HF15G2. FIG. 1J. Cp thermal shift profile for hit compound HF21E4. FIG. 1K. Cp thermal shift profile for hit compound HF25D7. FIG. 1L. HepAD38 cells were treated with hit compounds (10 µM), ETV (2.5 nM), or Bay 38-7690 (500 nM) and assessed for HBV DNA production. Dotted lines indicate no change and 50% reduction compared to the DMSO control.

DETAILED DESCRIPTION OF INVENTION

Figure 1A:
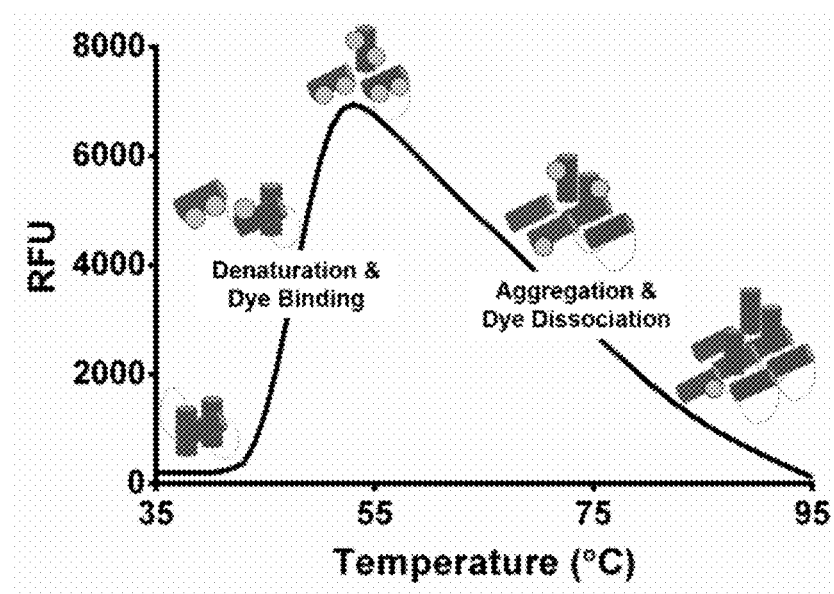
FIG. 1A-FIG. 1L. Screening for Cp-binding antivirals.

More than 240 million people worldwide are chronically infected with HBV, and there are an estimated 0.5-1 million deaths per year due to HBV-related liver conditions. Current treatment options rarely cure infections, and patients must therefore receive drug regimens of indefinite length, often lifelong. Furthermore, although combination regimens have proven very successful in treatment of other viral infections, such as HIV and hepatitis C virus, drug combinations are not possible in HBV treatments due to a lack of multiple drug classes.

As described above, current HBV treatment options are limited, and include only nucleoside reverse transcriptase inhibitors (NRTIs) and the immunomodulatory agent interferon alpha (IFN-α). However, both of these HBV treatment options have severe drawbacks. NRTIs often result in the viral load of patients rebounding after cessation of treatment. IFN-α treatment leads to numerous adverse side effects, such as depression, paraesthesia, myelosuppression, neutropenia, thrombocytopenia, abdominal discomfort, rash, pruritis, alopecia, thyroiditis, and influenza-like symptoms such as fatigue, headaches and weight loss.

The viral capsid protein (Cp) has recently gained attention as a possible therapeutic target because of its vital roles in the HBV life cycle. Reverse transcription occurs exclusively inside the viral capsid, and the capsid is required for nuclear entry of rcDNA. Cp has many more functions for pathogenicity of HBV, including roles in innate immune evasion and host manipulation. Cp has also been reported to interact with cccDNA, influencing epigenetic modifications and transcriptional activity, but the effects of these cccDNA-Cp interactions are not fully understood. Three main classes of capsid assembly effectors (CAEs) have been described in detail: heteroaryldyhydropyrimidines (HAPs), phenylpropenamides (PPAs), and sulfamoylbenzamides (SBAs). HAPs, PPAs, and SBAs all increase capsid assembly rate, but inhibit HBV replication by distinct mechanisms.

The present disclosure provides a new class of HBV CAEs that act with a novel mechanism. The presently disclosed optimized chemical entities act as potent inhibitors of HBV replication by affecting the roles of capsid protein in the viral life cycle. The presently disclosed compounds act by a novel mechanism that has not been reported, namely, they block the entry of HBV capsid protein into the cell nucleus. This prevents entry of HBV particles into the nucleus, thereby blocking viral genome amplification and preventing continued replication of the virus. The present disclosure thus provides novel therapeutic approaches to treat HBV. Given their novel mechanism of action, the presently disclosed compounds are also useful as a component in combination chemotherapy with existing anti-HBV agents. Importantly, the presently disclosed compounds demonstrate complementary resistance profiles to those of existing CAEs; specifically, viruses with mutations in the capsid gene that are resistant to current CAEs are sensitive to the presently disclosed compounds, and in some cases, hypersusceptible to the presently disclosed compounds.

Compounds

The compounds of the present disclosure comprise a new class of HBV capsid assembly effectors (CAEs). The presently disclosed compounds block the entry of HBV capsid protein into the cell nucleus, preventing entry of HBV particles into the nucleus, thereby blocking viral genome amplification and preventing continued replication of the virus. Thus, the presently disclosed compounds and methods are useful in the treatment or cure of HBV infection. Structures of certain exemplary compounds are shown in Table 2, below.

Formulations

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

Controlled-release (or sustained-release) preparations may be formulated to extend the activity of the agent(s) and reduce dosage frequency. Controlled-release preparations can also be used to effect the time of onset of action or other characteristics, such as blood levels of the agent, and consequently affect the occurrence of side effects. Controlled-release preparations may be designed to initially release an amount of an agent(s) that produces the desired therapeutic effect, and gradually and continually release other amounts of the agent to maintain the level of therapeutic effect over an extended period of time. In order to maintain a near-constant level of an agent in the body, the agent can be released from the dosage form at a rate that will replace the amount of agent being metabolized or excreted from the body. The controlled-release of an agent may be stimulated by various inducers, e.g., change in pH, change in temperature, enzymes, water, or other physiological conditions or molecules.

Agents or compositions described herein can also be used in combination with other therapeutic modalities, as described herein. Thus, in addition to the therapies described herein, one may also provide to the subject other therapies known to be efficacious for treatment of HBV infection.

Therapeutic Methods

Also provided are methods of treating HBV infection in a subject in need of thereof, comprising administration of a therapeutically effective amount of a compound described herein. Further discussion refers to compound HF9C6, but one of ordinary skill will understand that methods or compounds described herein can be used in conjunction with HF9C6 variants, which retain anti-HBV activity. Compounds and methods provided herein have the therapeutic potential to treat or reverse the symptoms of HBV infection.

Further, methods for prophylactic and therapeutic uses of the compounds described herein, as well as analogs of the described compounds, are provided herein. Disclosed herein are methods for the selection of candidates for prophylactic or therapeutic applications. First, a comprehensive structure-activity relationship (SAR) through exhaustive characterization of medicinal chemistry space can be established around compound HF9C6, including, but not limited to, understanding the functionalities that lead to improved potency while keeping candidates non-toxic and soluble. Second, non-toxic, orally available, and metabolically stable compounds that are effective against HBV infection can be identified.

Methods described herein are generally performed on a subject in need thereof. A subject in need of the therapeutic methods described herein can be a subject having, diagnosed with, suspected of having, or at risk for developing HBV infection. A determination of the need for treatment will typically be assessed by a history and physical exam consistent with the disease or condition at issue. Diagnosis of the various conditions treatable by the methods described herein is within the skill of the art. The subject can be an animal subject, including a mammal, such as horses, cows, dogs, cats, sheep, pigs, mice, rats, monkeys, guinea pigs, and chickens, and humans. For example, the subject can be a human subject. An effective amount of a compound described herein is generally that which can eliminate or reduce the effects of HBV infection in a subject.

When used in the treatments described herein, a therapeutically effective amount of compound described herein can be employed in pure form or, where such forms exist, in pharmaceutically acceptable salt form and with or without a pharmaceutically acceptable excipient. For example, the compounds of the present disclosure can be administered, at a reasonable benefit/risk ratio applicable to any medical treatment, in a sufficient amount to inhibit HBV replication.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the patient; the time of administration; the route of administration; the rate of excretion of the composition employed; the duration of the treatment; drugs used in combination or coincidental with the specific compound employed; and like factors well known in the medical arts (see, e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Administration of a compound described herein can occur as a single event or over a time course of treatment. For example, a compound described herein can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

A compound described herein can be administered simultaneously or sequentially with another agent, such as an antibiotic, an anti-inflammatory, or another agent, such as another antiviral compound. For example, a compound described herein can be administered simultaneously with another agent, through administration of separate compositions, each containing one or more of a compound described herein and another agent. Simultaneous administration can occur through administration of one composition containing two or more of a compound described herein, or another agent. A compound described herein can be administered sequentially with another agent. For example, a compound described herein can be administered before or after administration of another agent.

Additional AntiViral Compounds

The compounds described herein can also be used in combination with other antiviral compounds in the therapeutic methods as described herein. Such antiviral compounds include, but are not limited to, HAPs and SBAs.

The prototype HAP, Bay 41-4109, was first described in 2003 (Deres, et al., *Science* 299:893-896, 2003). Although Bay 41-4109 was shown to inhibit the virus replication cycle in rodent models, it was found to be hepatotoxic in high doses. Additional HAPs have recently been described, including, but not limited to, HAP-1, morphothiadine mesilate (GLS-4), HAP-18, NVR-010-001-E2 (Cole, *Curr. Opin. Pharmacol.* 30:131-137, 2016) and HAP_R01 (Zhou, et al., *Sci. Rep.* 7:42374, 2017). GLS-4 is a derivative of Bay 41-4109 that has been shown to be effective and much less toxic to primary human hepatocytes in preclinical studies (Wu, et al., *Antimicrob. Agents Chemother.* 57:5344-5354, 2013).

Another class of antiviral compounds that can be used in combination with the compounds of the present disclosure is SBAs. The SBAs were originally described as inhibiting assembly of HBV nucleocapsids in 2013 (Campagna, et al., *J. Virol.* 87:6931-6942, 2013). More recently, additional SBAs have been identified, including, but not limited to, SBA_R01 (Zhou, supra, 2017).

Administration

Agents and compositions described herein can be administered according to methods described herein in a variety of means known to the art. The agents and composition can be used therapeutically either as exogenous materials or as endogenous materials. Exogenous agents are those produced or manufactured outside of the body and administered to the body. Endogenous agents are those produced or manufactured inside the body by some type of device (biologic or other) for delivery within or to other organs in the body.

Administration can include, for example, methods involving oral ingestion, direct injection (e.g., systemic or stereotactic), drug-releasing biomaterials, polymer matrices, gels, permeable membranes, osmotic systems, multilayer coatings, microparticles, implantable matrix devices, mini-osmotic pumps, implantable pumps, injectable gels and hydrogels, liposomes, micelles (e.g., up to 30 µm), nanospheres (e.g., less than 1 µm), microspheres (e.g., 1-100 µm), reservoir devices, a combination of any of the above, or other suitable delivery vehicles to provide the desired release profile in varying proportions. Other methods of controlled-release delivery of agents or compositions will be known to the skilled artisan and are within the scope of the present disclosure.

Delivery systems may include, for example, an infusion pump which may be used to administer the agent or composition in a manner similar to that used for delivering insulin or chemotherapy to specific organs or tumors. Typically, using such a system, an agent or composition is administered in combination with a biodegradable, biocompatible polymeric implant that releases the agent over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

Agents can be encapsulated and administered in a variety of carrier delivery systems. Examples of carrier delivery systems include microspheres, hydrogels, polymeric implants, smart polymeric carriers, and liposomes (see generally, Uchegbu and Schatzlein, eds. (2006) Polymers in Drug Delivery, CRC, ISBN-10: 0849325331). Carrier-based systems for molecular or biomolecular agent delivery can: provide for intracellular delivery; tailor biomolecule/agent release rates; increase the proportion of biomolecule that reaches its site of action; improve the transport of the drug to its site of action; allow co-localized deposition with other agents or excipients; improve the stability of the agent in vivo; prolong the residence time of the agent at its site of action by reducing clearance; decrease the nonspecific delivery of the agent to non-target tissues; decrease irritation caused by the agent; decrease toxicity due to high initial doses of the agent; alter the immunogenicity of the agent; decrease dosage frequency, improve taste of the product; or improve shelf life of the product.

Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to, compounds described herein. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Definitions

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a," "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims. Additionally, citation of a reference herein shall not be construed as an admission that such is prior art to the present disclosure.

EXAMPLES

The following non-limiting examples are provided to further illustrate the present disclosure. It should be appreciated by those of skill in the art that the techniques disclosed in the examples that follow represent approaches the inventors have found function well in the practice of the present disclosure, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the present disclosure.

Example 1: Compounds and Reagents

Bay 38-7690 was synthesized by previously described protocols (Deres, et al., supra, 2003; Stray, et al., *Proc. Natl. Acad. Sci. USA* 102:8138-8143, 2005; Weber, et al., *Antiviral Res.* 54:69-78, 2002; Stoltefuss, et al., "Use of dihydropyrimidines as medicaments, and novel substances," Bayer Aktiengesellschaft, 2002 (Leverkusen, DE); Stoltefuss, et al., "New dihydropyrimidine derivatives and their corresponding mesomers useful as antiviral agents," 1999, Bayer AG). The Maybridge HITFINDER™ chemical library of compounds (version 6) was purchased from Maybridge (Thermo Fisher Scientific, Cornwall, United Kingdom). Lamivudine (3TC) was obtained through the U.S. NIH AIDS Reagent Program. Entecavir (ETV) was purchased from Sigma-Aldrich (St. Louis, Mo.).

Example 2—HBV Cp Purification

A gBlock Gene Fragment coding for the 149 amino acid assembly domain of HBV capsid protein with an added C-terminal cysteine (C150) with NdeI and BamHI restriction sites was synthesized by Integrated DNA Technologies (Coralville, Iowa) and cloned into the pET11a expression vector (Novagen, Billerica, Mass.). HBV C150 was expressed and purified as previously described (Stray, et al., *Nat. Biotechnol.* 24:358-362, 2006; Zlotnick, et al., *Nat. Protocols* 2:490-498, 2007; Zlotnick, et al., *Biochemistry* 35:7412-7421, 1996), with minor modifications. The C150 expression plasmid was transformed into BL21 (DE3) *E. coli*, grown at 37° C. to an OD600 of ~0.8, and induced for 3 hours with 1 mM IPTG at 37° C. Cells were pelleted and resuspended in 50 mM Tris (pH 7.5), 1 mM EDTA, 20 mM 2-mercaptoethanol (2-ME), 1 mM PMSF, 150 µg/ml lysozyme, and 0.2 mg/ml DNase I. The suspension was incubated on ice for 30 minutes and lysed by sonication. Polyethylenimine (PEI) was added to a final concentration of 0.15% w/v to precipitate DNA, and the lysate was centrifuged at 16,000×g for 1 hour. Ammonium sulfate was added to the supernatant to 40% saturation. The solution was gently stirred for 1 hour, then centrifuged at 16,000×g for 1 hour. The pellet was resuspended in Buffer A [100 mM Tris (pH 7.5), 100 mM NaCl, 10 mM 2-ME] to ~10 mg/ml, centrifuged at 16,000×g for 20 minutes, loaded onto a Buffer A-equilibrated HiLoad 26/60 Superdex 200 prep grade (GE Healthcare; Pittsburgh, Pa.) column, and eluted at 2.5 ml/min. Fractions were pooled based on the chromatogram and SDS-PAGE, concentrated to ~5 mg/ml, and dialyzed into Buffer N [50 mM sodium bicarbonate (pH 9.6), 10 mM 2-ME]. Solid urea was added to 3 M and stirred for 1 hour at 4° C. The solution was loaded onto a Buffer N-equilibrated HiLoad 26/60 Superdex 200 prep grade column and eluted at 2.5 ml/min. Fractions containing the C150 dimer (C150$_2$) were pooled, concentrated, and stored at −80° C. Final protein concentration was determined spectrophotometrically using an extinction coefficient of 60,900 (Zlotnick, et al., supra, 2007).

Example 3—Thermal Shift Screening Assay

The development and use of the thermal shift assay for drug discovery has been described previously (Lo, et al., *Anal. Biochem.* 332:153-159, 2004; Pantoliano, et al., *J. Biomolec. Screen.* 6:429-440, 2001). In a final reaction volume of 20 µl, 10 µl of C150$_2$ (15 µM) in Buffer N was mixed with 10 µl assembly buffer [100 mM HEPES (pH 7.5), 1 M NaCl] containing 2x SYPRO® Orange Protein Gel Stain (Life Technologies, Carlsbad, Calif.). Compounds were added at a final concentration of 20 µM, and reactions contained 1% DMSO. Samples were heated in a PIKO-REAL™ Real-Time PCR System (Thermo Fisher Scientific, Waltham, Mass.) from 25° C. to 95° C. in steps of 1° C. every 50 seconds. Melting curves were analyzed with PIKO-REAL™ Software.

Example 4—Cell Culture and Viruses

HepAD38 cells (ATCC; Ladner, et al., *Antimicrob. Agents Chemother.* 41:1715-1720, 1997) were maintained in tet media [Dulbecco's Modified Eagle Medium (DMEM) and 10% fetal bovine serum (FBS) plus 0.4 µg/ml tetracycline (tet) and 400 µg/ml G418 (Gibco; Gaithersburg, Md.)]. Cells were incubated at 37° C. with 5% $CO_2$.

Example 5—Quantitative Polymerase Chain Reaction Analysis of HBV Nucleic Acids

Total DNA from HBV-infected cells was extracted using the QIAamp DNA Blood Mini Kit (Qiagen, Germantown, Md.). Forward and reverse primers for total HBV DNA quantification were 5'-CCTGGTTATCGCTGGATGTGT-3' (SEQ ID NO:1) and 5'-GGACAAACGGGCAACATAC-CTT-3' (SEQ ID NO:2), respectively (Sitnik, et al., *Revista do Instituto de Medicina Tropical de Sao Paulo* 52:119-124, 2010). Amplification was conducted by denaturation at 95° C. for 10 min, followed by 40 cycles of denaturation at 95° C. for 15 s and annealing/extension at 60° C. for 1 min using PerfeCTa SYBR® Green FastMix reaction cocktail (Quanta Biosciences, Beverly, Mass.). Amplification was carried out in a PIKOREAL™ Real-Time PCR System. A standard curve was generated with dilutions of the HBV genome-containing plasmid pCMV-HBV-LE-II (Tavis, et al., *PLoS Pathogens* 9:e1003125, 2013).

Example 6—Antiviral Screening

HepAD38 cells ($5 \times 10^4$) were plated in 96-well plates in tet media. The next day, cells were washed 2× with PBS, and the media was replaced with complete media (DMEM, 10% FBS) containing compounds. Fresh complete media with compounds was added again after 2 days. After 2 additional days, cells were washed with PBS, trypsinized, and pelleted by centrifugation. The cell pellet was resuspended in 200 µl PBS, and DNA was extracted and analyzed as above. For dose responses, values were plotted in GraphPad Prism 5 and analyzed with the log (inhibitor) vs. normalized response—variable slope equation.

Example 7—Cytotoxicity

HepG2 cells were treated with compounds as in the antiviral screening above. At the end of treatment duration, cell viability was assessed with the Cell Proliferation Kit II (XTT) (Roche, Basel, Switzerland) according to the manufacturer's instructions. Values were plotted in GraphPad Prism 5 and analyzed with the log (inhibitor) vs. normalized response—variable slope equation.

Example 8—Western Blotting

Cells were lysed by addition of RIPA buffer [50 mM Tris (pH 7.5), 150 mM NaCl, 1 mM EGTA, 1 mM EDTA, 0.1% SDS, 1% Triton X-100] and incubated on ice for 30 min with occasional vortexing. The lysate was centrifuged at 14,000×g for 15 min, the supernatant was collected, and protein was quantitated by Bradford assay. Protein (8 µg) in laemmli buffer was separated by SDS-PAGE and transferred to PVDF Immobilon-P membranes (Millipore, Billerica, Mass.). Membranes were probed with rabbit anti-HBV core (Austral Biologicals, San Ramon, Calif.) (1:500 dilution) and mouse anti-GAPDH (Santa Cruz Biotechnology) (1:5,000) antibodies, followed by anti-mouse and anti-rabbit HRP-conjugated secondary antibodies (Sigma-Aldrich). Bound antibodies were visualized by adding Luminata Forte Western HRP substrate (Millipore) to the membrane and imaged with a Fuji camera system.

Example 9—Immunofluorescence

Cells were fixed at room temperature (RT) for 15 min in 4% formaldehyde, permeabiliied with 0.1% Triton X-100 in PBS, and blocked with 10% goat serum (Jackson ImmunoResearch, West Grove, Pa.) and 1% bovine serum albumin (BSA) in PBS. Rabbit anti-HBV core primary antibody (Dako, Santa Clara, Calif.) (1:1,000) was bound overnight at 4° C. Samples were incubated at RT for 45 min with 1:2,000 goat anti-rabbit ALEXA FLUOR® 568 secondary antibody (Invitrogen), stained with ACTINGREEN™ 488 stain (Life Technologies) according to the manufacturer's instructions, and stained for nuclei using HOECHST® 33342 (Invitrogen) or DRAQ5 (Thermo Scientific).

Example 10—Confocal Microscopy and Image Analysis

HepAD38 cells ($1 \times 10^4$) were seeded in 96-well 2% collagen-coated image plates (BD Falcon, Bedford, Mass.) in tet media. On the appropriate days, the cells were washed twice with PBS and complete media containing compounds was added to the wells with 1% final DMSO concentration. Cells were fixed and stained on the indicated days post-induction, and the protein redistribution was analyzed from confocal images taken with a Zeiss LSM 510 Meta confocal microscope with Autostage, Multitile, and MultiTime series 4.0.31 beta software, as previously described (Liu, et al., *Antimicrob. Agents Chemother.* 59:3482-3492, 2015). Imaging was carried out using a 40× objective, capturing 9 images per well. Images were processed using CellProfiler software (Kamentsky, et al., *Bioinformatics* 27:1179-1180, 2011; Carpenter, et al., *Genome Biology* 7:R100, 2006; Lamprecht, et al., *BioTechniques* 42:71-75, 2007). Additional images were taken on a confocal laser scanning Leica TCS SP8 microscope.

Example 11—Dot Blot HBV DNA Assay

The dot blot assay was performed similarly to previously described (Campagna, et al., supra,2013, Qiu, et al., *J. Med. Chem.* 59:7651-7666, 2016). HepAD38 cells were seeded in 96- well plates ($3 \times 10^4$ cells/well) in tet media. The following day, the cells were washed 2× with PBS and complete media containing 2-fold serial dilutions of test compounds was added to the wells with 1% final DMSO concentration. After 2 days, the media was removed, and fresh media containing compounds was added. After 2 additional days, cells were washed with PBS and lysed with 10 mM Tris (pH 7.5), 1mM EDTA, 100mM NaCl, 1% NP-40 at 37° C. for 30 min. 60 µl of lysate was added to 60 µl of 1 M NaOH, 1.5 M NaCl and incubated at RT for 5 min to denature DNA. 120 µl of 1 M Tris (pH 7.4), 2 M NaCl was added. Samples were transferred to positively charged nylon membranes (Roche) using a vacuum dot blot manifold. The wells were washed with 200 µl of 20× SSC (3M NaCl, 300 mM sodium citrate), and the DNA was UV crosslinked to the membranes. The membrane was subjected to Southern blot using a 500 base pair digoxigenin (DIG)-labeled HBV-specific probe synthesized from HepAD38 cells using 5'-GGCCTTTCTGTG-TAAACAATACCTGAACC-3' (SEQ ID NO:3) and 5'-GTAATCGAGCTCCGGTGGTCTCCATGCGAC-3' (SEQ ID NO:4) primers with the PCR DIG Probe Synthesis Kit (Roche), as described previously (Huber, et al., *Antimicrob. Agents Chemother.* 61; e00245-17, 2017). Membranes were incubated with CDP-STAR® chemiluminescent substrate (Roche), imaged by chemiluminescence, and quantified by densitometry. Values were plotted in GraphPad Prism 5 and analyzed with the log (inhibitor) vs. normalized response—variable slope equation.

Figure 1B:
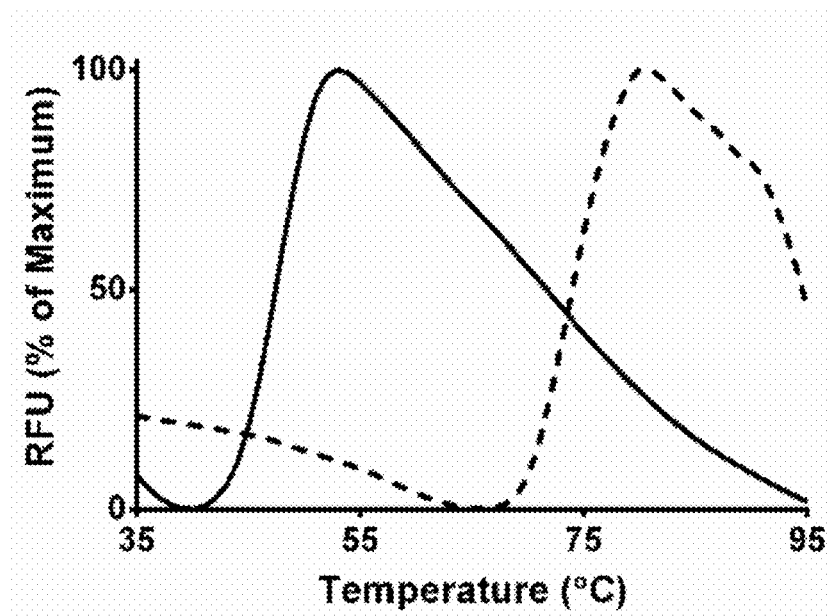
Figure 1C:
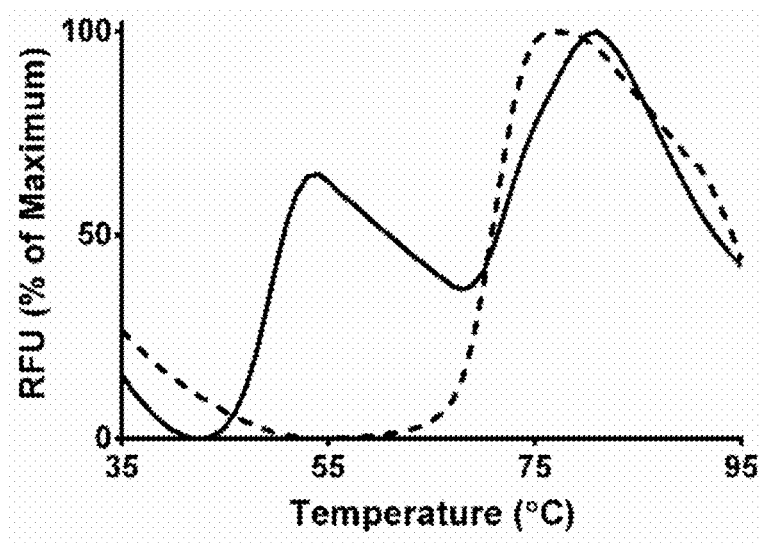
Figure 1D:
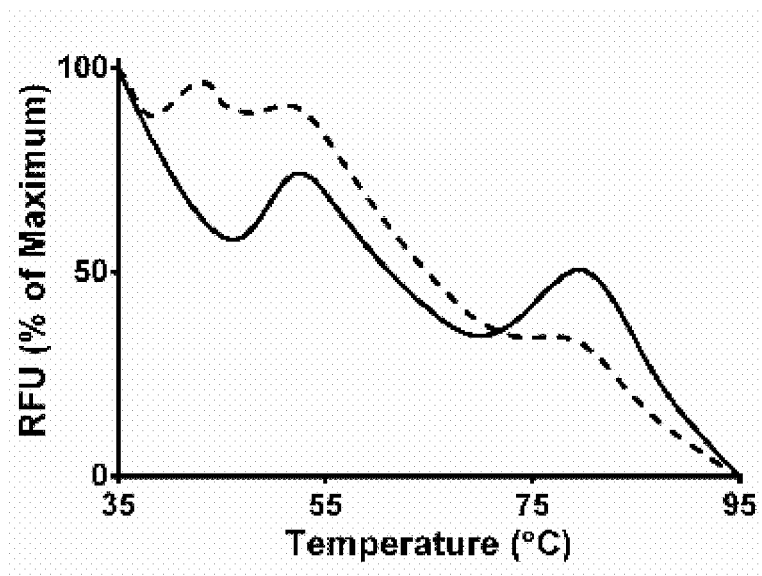
Figure 1E:
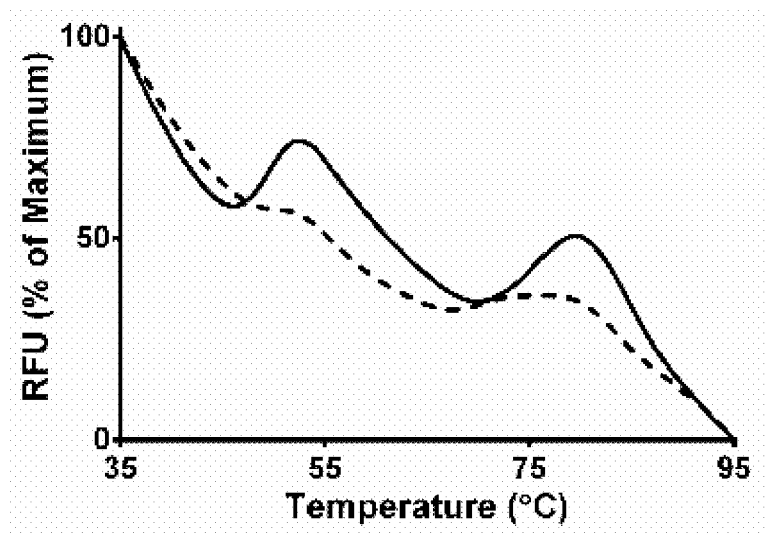
Figure 1F:
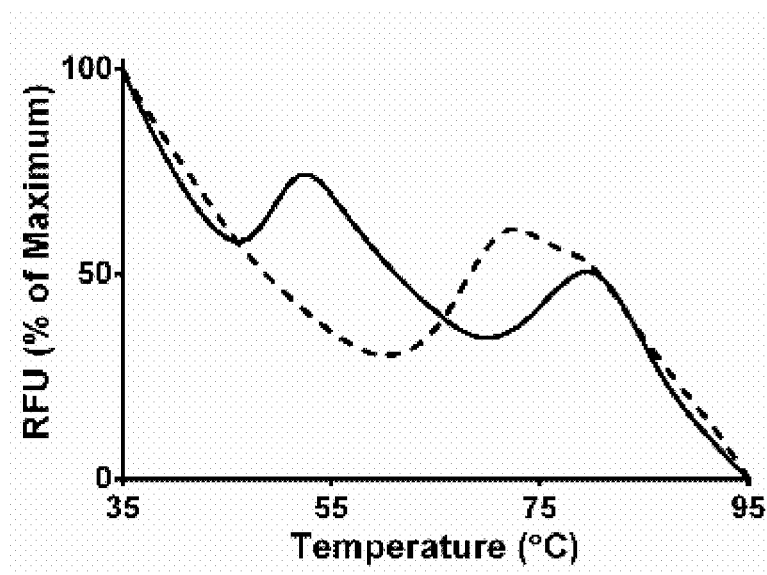
Figure 1G:
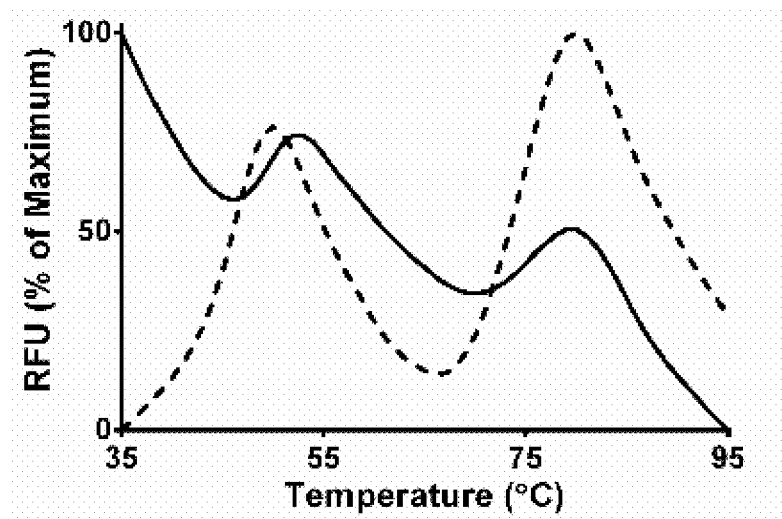
Figure 1H:
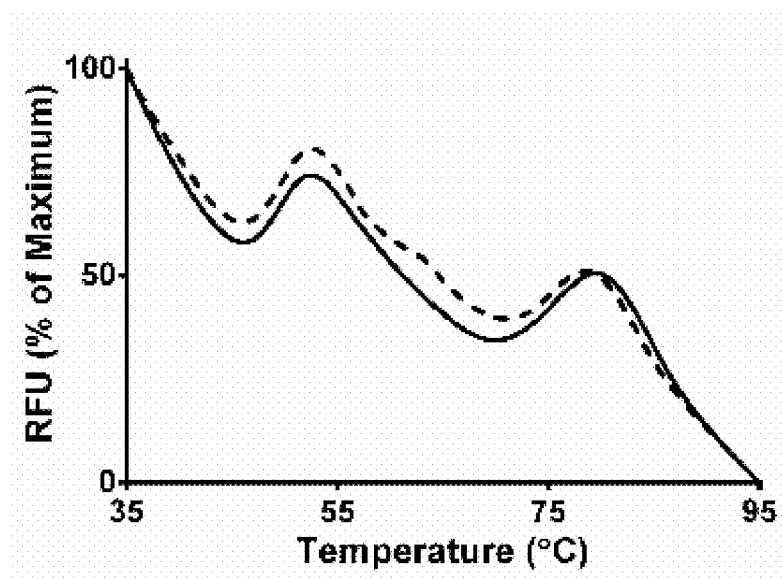
Figure 1I:
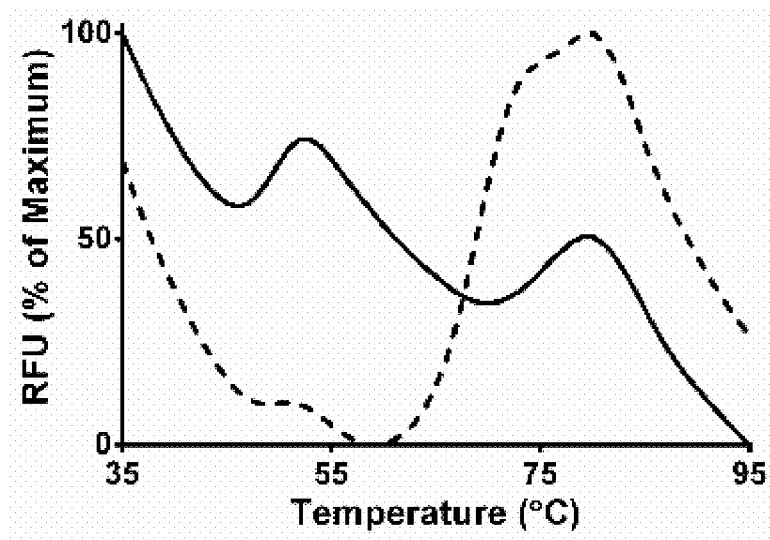
Figure 1J:
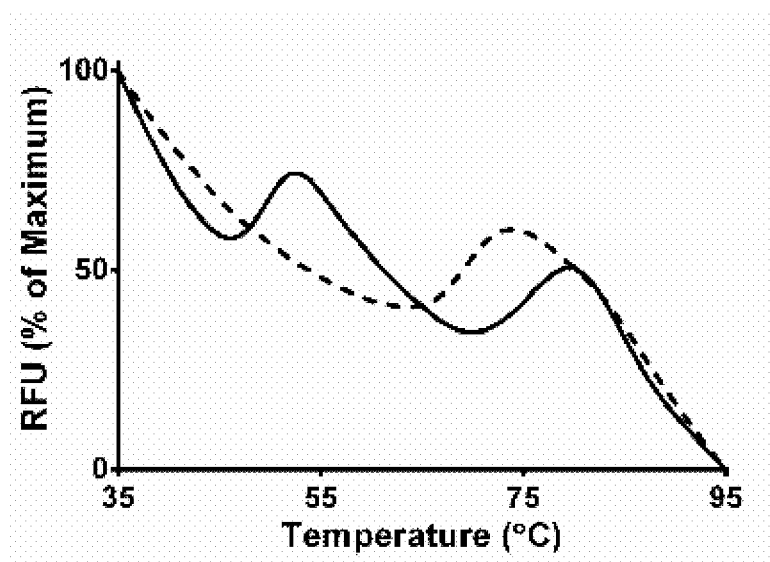
Figure 1K:
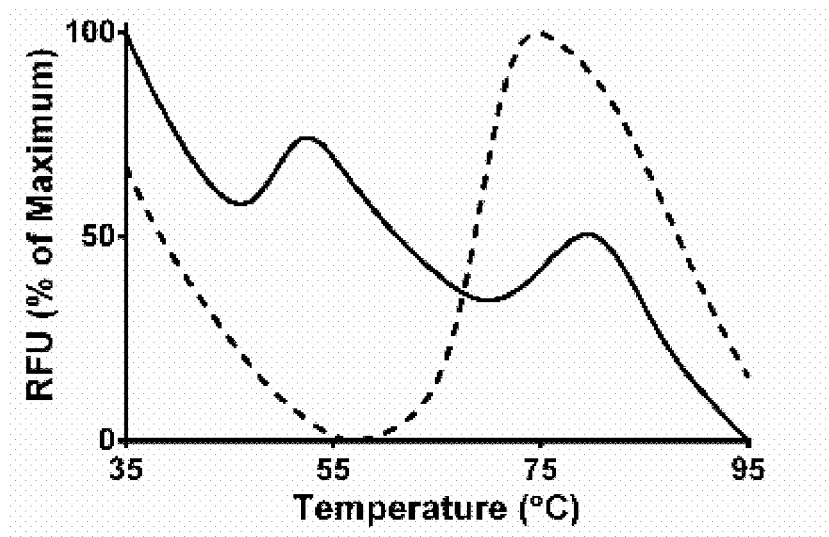

Example 12—Development of Thermal Shift Screening Assay and Compound Screening A schematic of the thermal shift assay (TSA) is shown in FIG. 1A. Conditions for TSA were optimized according to signal-to-noise ratio and ease of discerning hit compounds from non-Cp-binding compounds. Ranges of C1502 concentrations (2.5-20 µM), pH (7.0-9.6), NaCl (0.5-2.5 M), and SYPRO® Orange dye (1×-5×) were tested. Furthermore, incubation conditions were tested before thermal denaturation. Pre-incubation times of 0-30 min at 25° C. and 37° C. were tested. Non-assembly conditions (pH 9.6, no NaCl, no pre-incubation) yielded mainly one denaturation peak with a melting temperature ($T_m$) of 48° C., while full assembly conditions (pH 7.5, 0.5 M NaCl, 30 min pre-incubation at 37° C.) yielded one denaturation peak with $T_m$=75° C. (FIG. 1B). To maximize potential for finding hit compounds, conditions were chosen that allowed both peaks to be seen; with this method, $T_m$ shifts can be seen on both denaturation peaks. The chosen conditions were 0.5 M NaCl, pH 7.5, and 1× SYPRO® Orange dye with no pre-incubation. Final thermal cycling parameters are shown herein above.

Compounds were screened at 20 µM final concentration, and melting curves were analyzed for $T_m$ shifts or changes in the ratio of peak 1 to peak 2. Representative graphs for DMSO (negative control), Bay 38-7690 (positive control), and assorted hit/non-hit compounds are shown in FIG. 1C-FIG. 1K. Approximately 50 hits were found in a screen of ~4,000 compounds from the Maybridge HITFINDER™ chemical library of compounds (version 6), a hit rate of ~1.25%.

Example 13—Antiviral Screening of Hit Compounds

Figure 1L:
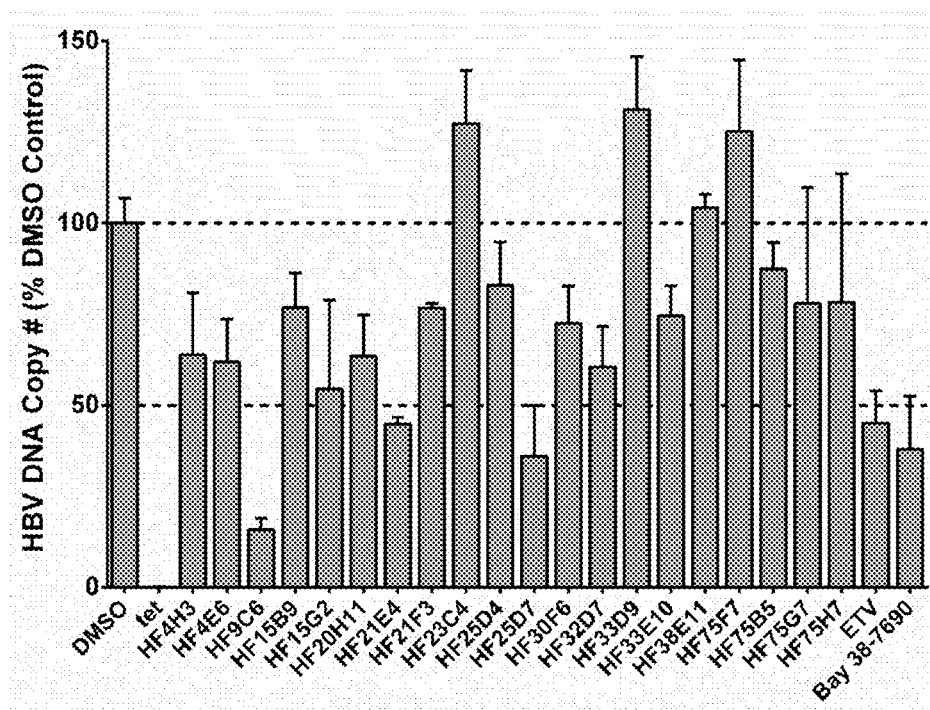

For antiviral screening, HepAD38 cells were treated with 10 µM of each hit compound, and anti-HBV activity was determined by the level of viral DNA. While many compounds significantly reduced HBV DNA, HF9C6 had the greatest effect (~80% reduction) (FIG. 1L).

Example 14—Antiviral Activity of HF9C6

Based on the screening results in FIG. 1D—FIG. 1L, HF9C6 was selected for further analysis. Dose responses using total intracellular HBV DNA as a marker and cytotoxicity with the XTT assay were conducted for HF9C6, and Bay 38-7690 and 3TC as controls, in HepAD38 cells (Table 1; $EC_{50}$, Half Maximal Effective Concentration; $CC_{50}$, Cytotoxic Concentration 50; SI, Selectivity Index).

TABLE 1

| Compound | $EC_{50}$ (µM) | $CC_{50}$ (µM) | SI |
|---|---|---|---|
| HF9C6 | 3.6 ± 0.2 | >300 | >83 |
| Bay 38-7690 | 0.6 ± 0.2 | >100 | >167 |
| Lamivudine (3TC) | 0.09 ± 0.01 | >100 | >1,111 |

Figure 2:
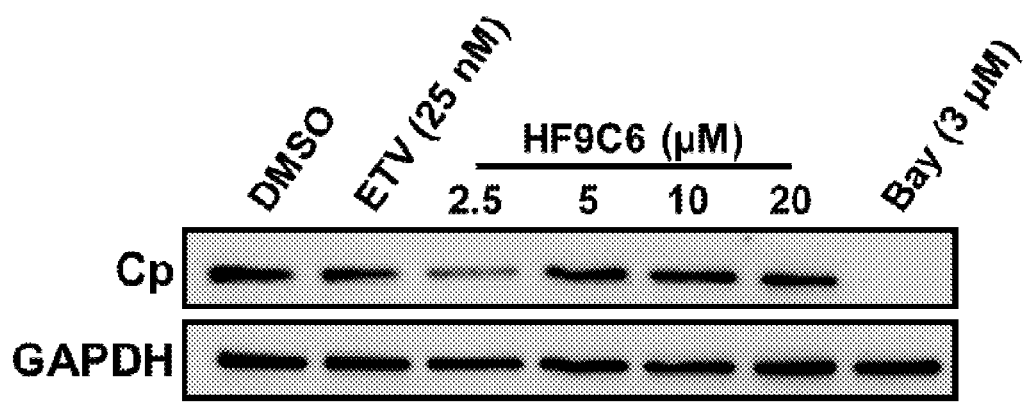
FIG. 2. HF9C6 does not induce Cp degradation. HepAD38 cells were treated with ETV (25 nM), Bay 38-7690 (3 µM), or the indicated concentrations of HF9C6. Cells were lysed, and the lysate was subjected to SDS-PAGE followed by Western blot analysis.

HAPs have been shown to induce intracellular degradation of Cp by way of the proteasome (Deres, et al., supra, 2003). To test if HF9C6 has the same effect, HepAD38 cells were induced and treated with HF9C6 and Bay 38-7690. While Bay 38-7690 completely eliminated Cp at 3 µM (5×$EC_{50}$), HF9C6 did not reduce Cp levels at concentrations up to 20 µM (~5×$EC_{50}$) (FIG. 2).

In order to evaluate the effect of HF9C6 on capsid assembly in vitro, C1502 (10 µM) was assembled in the presence or absence of HF9C6 (20 µM) or Bay 38-7690 (5 µM) and analyzed by transmission electron microscopy (TEM) similarly as previously described (Stray, et al., *JMR* 19:542-548, 2006; Bourne, et al., *J. Virol.* 82:10262-10270, 2008; Zlotnick, et al., *J. Virol.* 76:4848-4854, 2002). Capsids assembled in the presence of the carrier DMSO were spherical, ~40 nm in diameter, and dispersed across the TEM grid. Capsids assembled in the presence of Bay 38-7690 were inflated and misshapen. Capsids assembled in the presence of HF9C6, however, were heterogeneous in shape and size, and formed large aggregates on the grid.

Figure 3A:
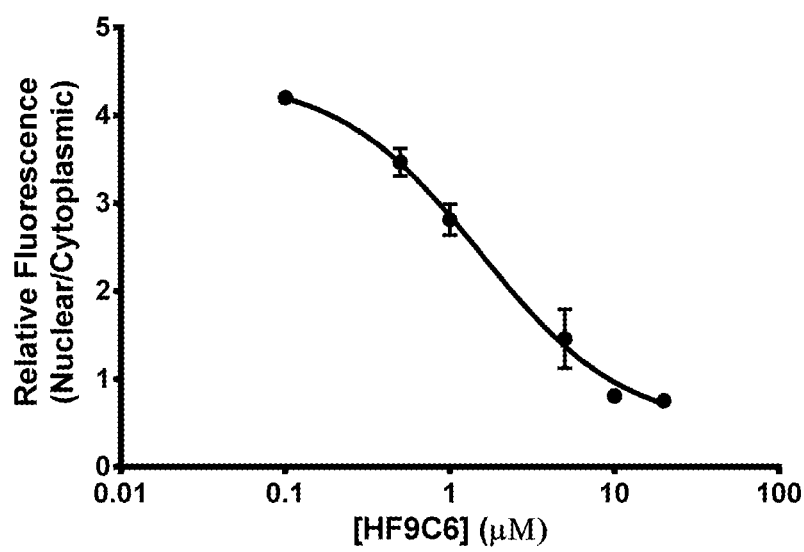
FIG. 3A and FIG. 3B. Quantification of Cp localization upon compound treatment. HepAD38 cells were induced in the presence of increasing amounts of HF9C6 (FIG. 3A) or Bay 38-7690 (FIG. 3B), stained for Cp after 5 days, imaged as described in the Examples section, below, and the amounts of nuclear and cytoplasmic Cp were quantified with CellProfiler. The values represent mean±standard error of the mean from two independent experiments.
Figure 3B:
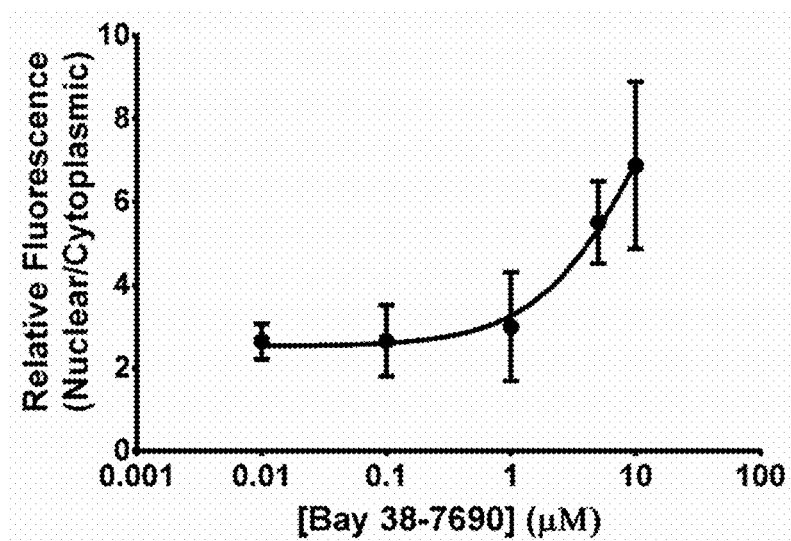

Next, the effect of HF9C6 treatment on Cp aggregation in HepAD38 cells was studied. HBV production was induced by tet withdrawal, and cells were treated with either DMSO, HF9C6 (20 µM), or Bay 38-7690 (5 µM), fixed, and stained for Cp, nuclei, and F-actin. DMSO-treated cells had an even dispersion of Cp throughout the cell, while Cp in HF9C6-treated cells was concentrated in large foci throughout the cell. Surprisingly, while Cp in DMSO-treated samples was spread throughout both the cytoplasm and nucleus, Cp in HF9C6-treated cells was excluded from the nucleus. These results suggest that HF9C6-mediated aggregation of Cp inhibits nuclear entry of virions, a process that is required for HBV infection and cccDNA amplification. This effect is hugely different from that observed with treatment with Bay 38-7690, as Bay 38-7690 induces Cp aggregates inside the nucleus rather than outside (FIG. 3A and FIG. 3B).

Example 15—Development of Potent HF9C6 Analogs

Due to the moderate potency and interesting mechanistic properties of HF9C6, while showing no observable cytotoxicity, 60 analogs of HF9C6 were synthesized to improve the antiviral properties. The chemical structures and TSA and cell-based results are summarized in Table 2.

The general synthetic schemes are shown below:

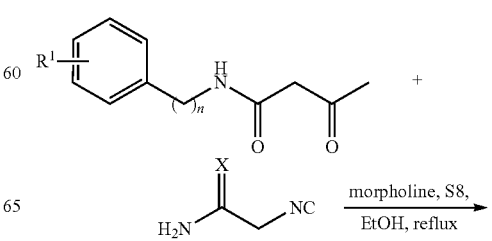

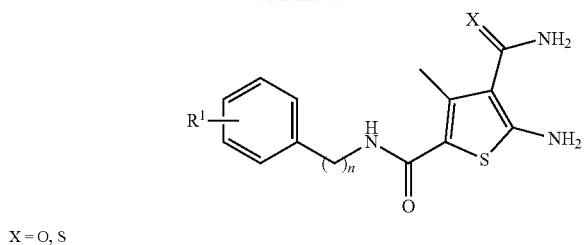
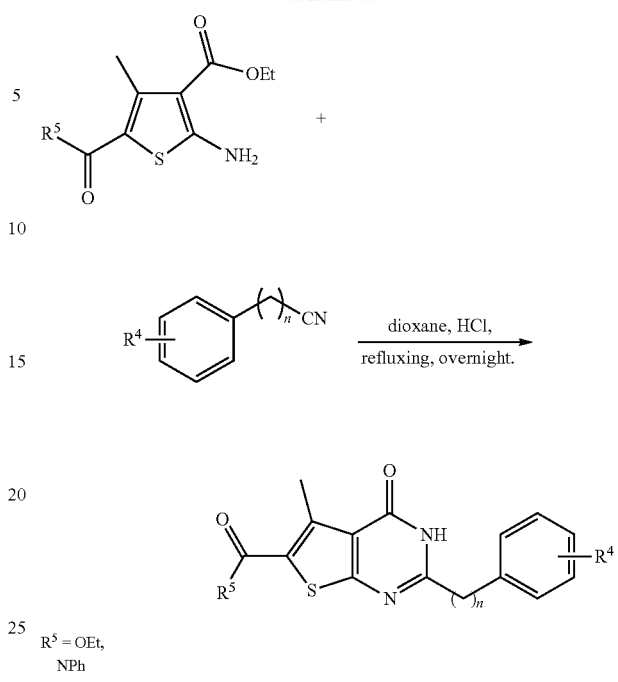
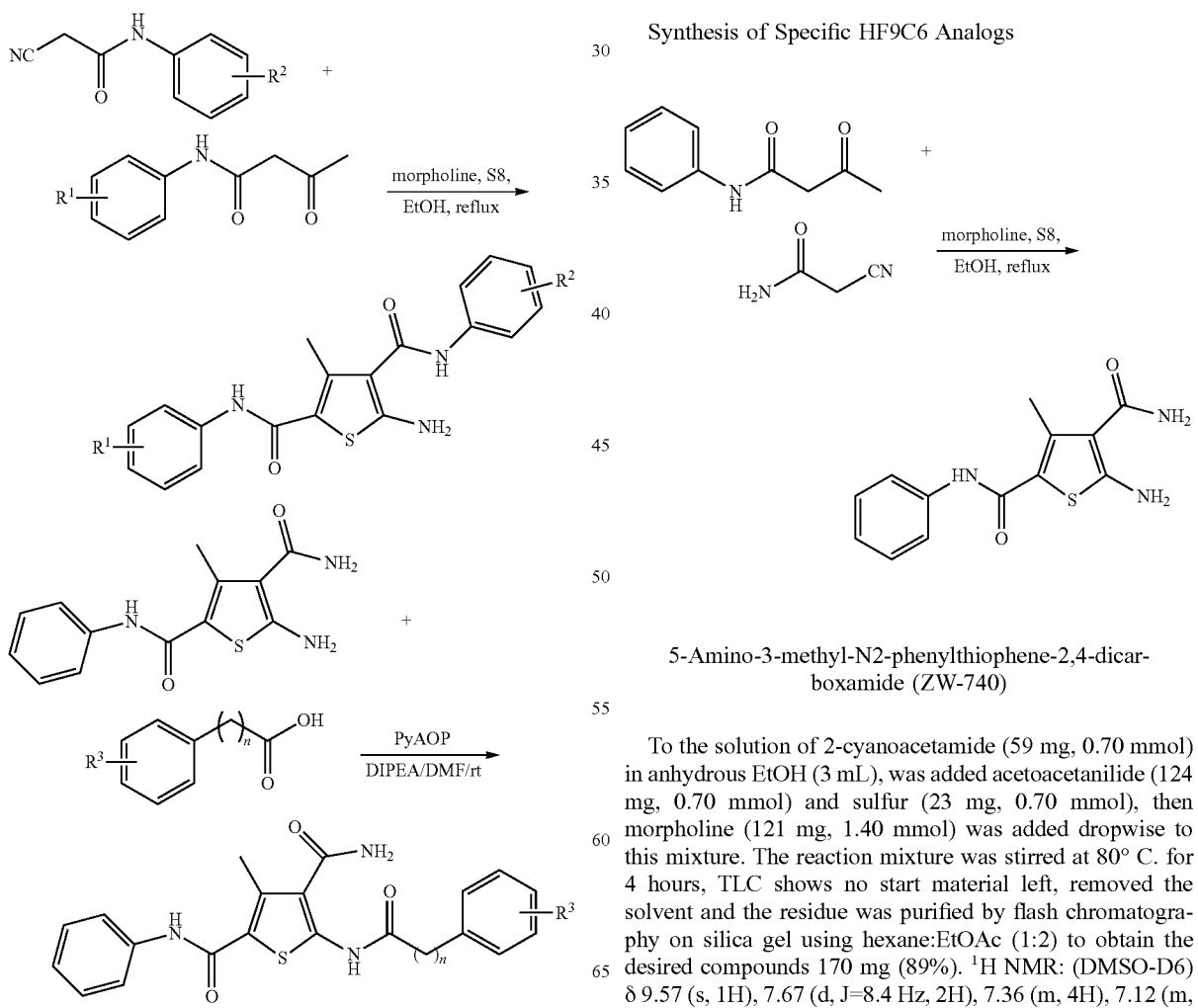

Synthesis of Specific HF9C6 Analogs

5-Amino-3-methyl-N2-phenylthiophene-2,4-dicarboxamide (ZW-740)

To the solution of 2-cyanoacetamide (59 mg, 0.70 mmol) in anhydrous EtOH (3 mL), was added acetoacetanilide (124 mg, 0.70 mmol) and sulfur (23 mg, 0.70 mmol), then morpholine (121 mg, 1.40 mmol) was added dropwise to this mixture. The reaction mixture was stirred at 80° C. for 4 hours, TLC shows no start material left, removed the solvent and the residue was purified by flash chromatography on silica gel using hexane:EtOAc (1:2) to obtain the desired compounds 170 mg (89%). $^1$H NMR: (DMSO-D6) δ 9.57 (s, 1H), 7.67 (d, J=8.4 Hz, 2H), 7.36 (m, 4H), 7.12 (m, 1H), 7.05 (s, 2H), 2.41 (s, 3H).

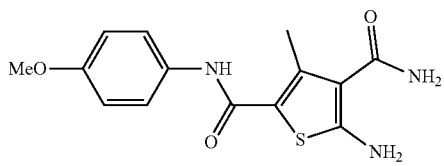 [SMILES: COc1ccc(NC(=O)c2sc(N)c(C(N)=O)c2C)cc1]

5-Amino-N2-(4-methoxyphenyl)-3-methylthiophene-2,4-dicarboxamide (ZW-769)

¹H NMR: (DMSO-D$_6$) δ 9.56 (s, 1H), 7.63 (d, J=8.4 Hz, 2H), 7.42 (s, 2H), 7.21 (d, J=8.4 Hz, 2H), 7.05 (s, 2H), 3.98 (s, 3H), 2.45 (s, 3H).

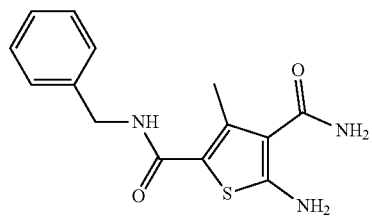 [SMILES: Cc1c(C(=O)NCc2ccccc2)sc(N)c1C(N)=O]

5-Amino-N2-benzyl-3-methylthiophene-2,4-dicarboxamide (ZW-770)

¹H NMR: (DMSO-D$_6$) δ 8.00 (s, 1H), 7.30 (t, J=7.8 Hz, 2H), 7.25 (d, J=7.8 Hz, 2H), 7.20 (t, J=7.2 Hz, 1H), 7.13 (s, 2H), 6.91 (s, 2H), 4.32 (s, 2H), 2.43 (s, 3H).

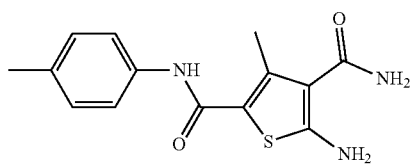

5-Amino-3-methyl-N2-(p-tolyl)thiophene-2,4-dicarboxamide (ZW-771)

¹H NMR: (DMSO-D$_6$) δ 9.48 (s, 1H), 7.55 (d, J=8.4 Hz, 2H), 7.36 (s, 2H), 7.17 (d, J=8.4 Hz, 2H), 7.03 (s, 2H), 2.56 (s, 3H), 2.32 (s, 3H).

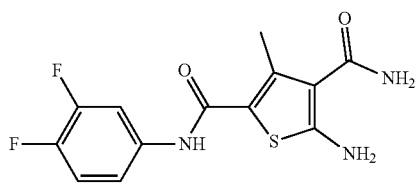 [SMILES: Cc1c(C(=O)Nc2ccc(F)c(F)c2)sc(N)c1C(N)=O]

5-Amino-N2-(3,4-difluorophenyl)-3-methylthiophene-2,4-dicarboxamide (ZW-896)

¹H NMR: (CD$_3$OD) δ 7.64 (m, 1H), 7.24 (m, 1H), 7.21 (m, 1H), 2.41 (s, 3H).

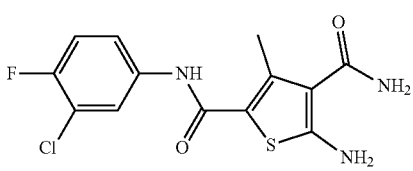 [SMILES: Cc1c(C(=O)Nc2ccc(F)c(Cl)c2)sc(N)c1C(N)=O]

5-Amino-N2-(4-fluoro-3-methylphenyl)-3-methylthiophene-2,4-dicarboxamide (ZW-935)

¹H NMR: (CD$_3$OD) δ 7.31 (d, J=6.0 Hz, 1H), 7.25 (m, 1H), 6.89 (t, J=8.4 Hz, 1H), 2.43 (s, 3H), 2.16 (s, 3H).

5-Amino-N2-(3-chloro-4,5-difluorophenyl)-3-methylthiophene-2,4-dicarboxamide (ZW-1034)

¹H NMR: (CD$_3$OD) δ 7.34 (s, 1H), 7.33 (s, 1H), 2.48 (s, 3H).

5-Amino-N2-(3-chloro-4-fluorophenyl)-3-methylthiophene-2,4-dicarboxamide (ZW-1035)

¹H NMR: (CD$_3$OD) δ 7.99 (d, J=9.0 Hz, 1H), 7.68 (m, 1H), 7.41 (t, J=9.0 Hz, 1H), 2.78 (s, 3H).

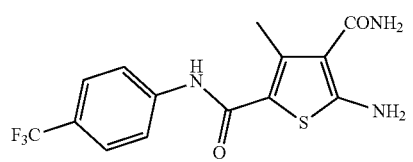 [SMILES: Cc1c(C(=O)Nc2ccc(C(F)(F)F)cc2)sc(N)c1C(N)=O]

5-Amino-3-methyl-N2-(4-(trifluoromethyl)phenyl)thiophene-2,4-dicarboxamide (ZW-1036)

¹H NMR: (CD$_3$OD) δ 8.05 (d, J=8.4 Hz, 2H), 7.91 (d, J=9.0 Hz, 2H), 2.87 (s, 3H).

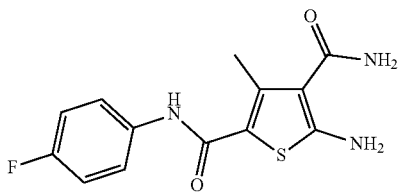 [SMILES: Cc1c(C(=O)Nc2ccc(F)cc2)sc(N)c1C(N)=O]

5-Amino-N2-(4-fluorophenyl)-3-methylthiophene-2,
4-dicarboxamide (ZW-1037)

¹H NMR: (DMSO-D₆) δ 9.62 (s, 1H), 7.69 (m, 2H), 7.35 (s, 2H), 7.21 (t, J=8.4 Hz, 2H), 7.02 (s, 2H), 2.47 (s, 3H).

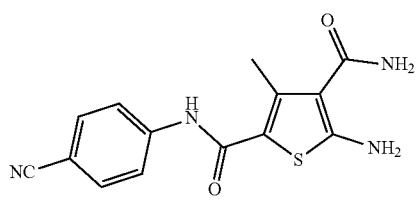 [SMILES: Cc1c(C(=O)Nc2ccc(C#N)cc2)sc(N)c1C(N)=O]

5-Amino-N2-(4-cyanophenyl)-3-methylthiophene-2,
4-dicarboxamide (ZW-1038)

¹H NMR: (DMSO-D₆) δ 9.98 (s, 1H), 7.86 (d, J=7.8 Hz, 2H), 7.81 d, J=7.8 Hz, 2H), 7.43 (s, 2H), 7.09 (s, 2H), 2.41 (s, 3H).

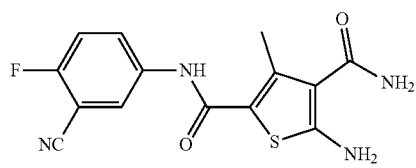

5-Amino-N2-(3-cyano-4-fluorophenyl)-3-methylthiophene-2,4-dicarboxamide (ZW-1039)

¹H NMR: (DMSO-D₆) δ 9.86 (s, 1H), 8.17 (m, 1H), 8.00 (m, 1H), 7.56 (t, J=9.0 Hz, 1H), 7.41 (s, 2H), 7.09 (s, 2H), 2.49 (s, 3H).

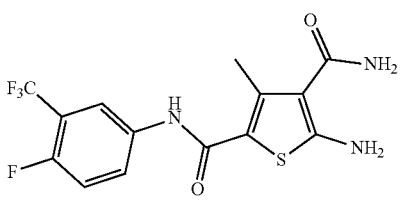 [SMILES: Cc1c(C(=O)Nc2ccc(F)c(C(F)(F)F)c2)sc(N)c1C(N)=O]

5-Amino-N2-(4-fluoro-3-(trifluoromethyl)phenyl)-3-methylthiophene-2,4-dicarboxamide (ZW-1057)

¹H NMR: (CD₃OD) δ 7.87 (d, J=6.0 Hz, 1H), 7.71 (m, 1H), 7.18 (t, J=9.6 Hz, 1H), 2.46 (s, 3H).

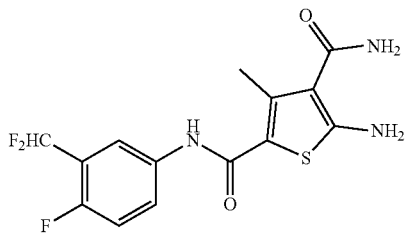 [SMILES: Cc1c(C(=O)Nc2ccc(F)c(C(F)F)c2)sc(N)c1C(N)=O]

5-Amino-N2-(3-(difluoromethyl)-4-fluorophenyl)-3-methylthiophene-2,4-dicarboxamide (ZW-1066)

¹H NMR: (CD₃OD) δ 7.75 (d, J=6.0 Hz, 1H), 7.62 (m, 1H), 7.11 (t, J=9.6 Hz, 1H), 6.96 (t, J=67.2 Hz, 1H), 2.43 (s, 3H).

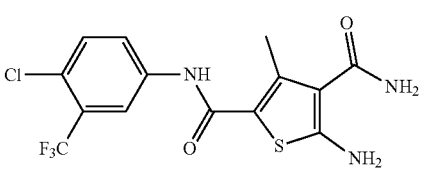 [SMILES: Cc1c(C(=O)Nc2ccc(Cl)c(C(F)(F)F)c2)sc(N)c1C(N)=O]

5-Amino-N2-(4-chloro-3-(trifluoromethyl)phenyl)-3-methylthiophene-2,4-dicarboxamide (ZW-1067)

¹H NMR: (CD₃OD) δ 8.02 (s, 1H), 7.46 (d, J=7.8 Hz, 1H), 7.46 (d, J=9.0 Hz, 1H), 2.53 (s, 3H).

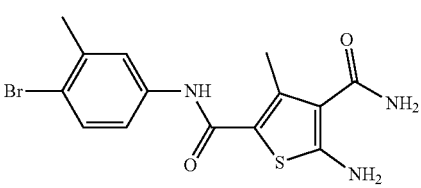 [SMILES: Cc1cc(NC(=O)c2sc(N)c(C(N)=O)c2C)ccc1Br]

5-Amino-N2-(4-bromo-3-methylphenyl)-3-methylthiophene-2,4-dicarboxamide (ZW-1068)

¹H NMR: (CD₃OD) δ 7.42 (d, J=8.4 Hz, 1H), 7.39 (d, J=9.0 Hz, 1H), 7.24 (dd, J=3.0, 9.0 Hz, 1H), 2.48 (s, 3H), 2.29 (s, 3H).

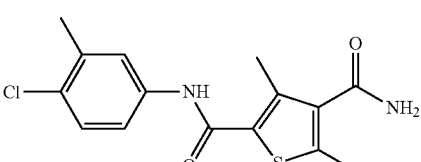

5-Amino-N2-(4-bromo-3-methylphenyl)-3-methylthiophene-2,4-dicarboxamide (ZW-1069)

¹H NMR: (CD₃OD) δ 7.38 (s, 1H), 7.29 (m, 1H), 7.19 (m, 1H), 2.47 (s, 3H), 2.26 (s, 3H).

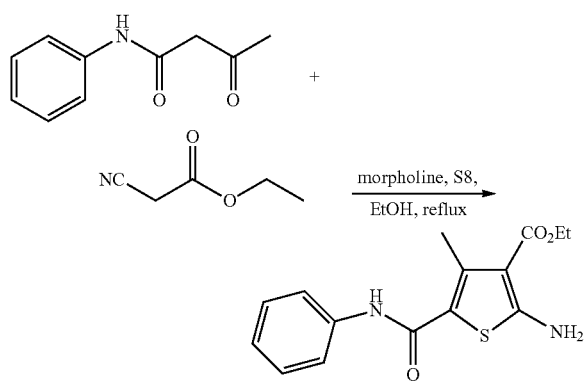

Ethyl 2-amino-4-methyl-5-(phenylcarbamoyl)thiophene-3-carboxylate. (ZW-1045)

To the solution of ethyl 2-cyanoacetate (0.5 mmol) (57 mg, 0.5 mmol) in anhydrous EtOH (2.0 mL), was added acetoacetanilide (89 mg, 0.5 mmol) and sulfur (16 mg, 0.5 mmol), then morpholine (1.0 mmol) was added dropwise to this mixture. The reaction mixture was stirred at 80° C. for 4 hours, TLC shows no start material left, removed the solvent and the residue was purified by flash chromatography on silica gel using hexane:EtOAc (1:1) to obtain the desired compounds 130 mg (87%). $^1$H NMR: (DMSO-D$_6$) δ 9.66 (s, 1H), 7.72 (s, 2H), 7.59 (d, J=7.2 Hz, 2H), 7.30 (t, J=7.8 Hz, 2H), 7.04 (t, J=7.2 Hz, 1H), 4.23 (q, J=6.6 Hz, 2H), 2.48 (s, 2H), 1.29 (t, J=6.6 Hz, 3H).

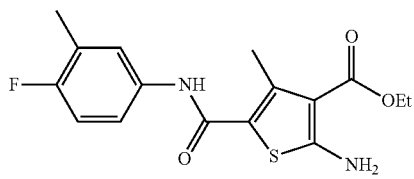 [SMILES: CCOC(=O)c1c(N)sc(C(=O)Nc2ccc(F)c(C)c2)c1C]

Ethyl 2-amino-5-((4-fluoro-3-methylphenyl)carbamoyl)-4-methylthiophene-3-carboxylate (ZW-1046)

$^1$H NMR: (CD$_3$OD) δ 7.31 (d, J=7.2 Hz, 1H), 7.26 (m, 1H), 6.89 (t, J=8.4 Hz, 1H), 4.22 (q, J=7.2 Hz, 2H), 2.48 (s, 2H), 2.16 (s, 3H), 1.27 (t, J=7.2 Hz, 3H).

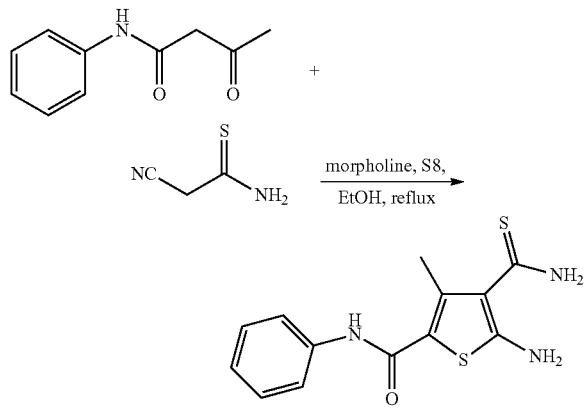

5-Amino-4-carbamothioyl-N-(3,4-difluorophenyl)-3-methylthiophene-2-carboxamide (ZW-1048)

To the solution of 2-cyanoacetamide (0.3 mmol) in anhydrous EtOH (1 mL), was added 2-cyanoethanethioamide (0.3 mmol), then morpholine (0.6 mmol) was added dropwise to this mixture. The reaction mixture was stirred at 80° C. for 4 hours, TLC shows no start material left, removed the solvent and the residue was purified by flash chromatography on silica gel using hexane:EtOAc (1:2) to obtain the desired compounds 51 mg (61%). $^1$H NMR: (CD$_3$OD) δ 7.64 (d, J=7.8 Hz, 2H), 7.44 (t, J=7.8 Hz, 2H), 7.23 (t, J=7.2 Hz, 1H), 2.56 (s, 3H).

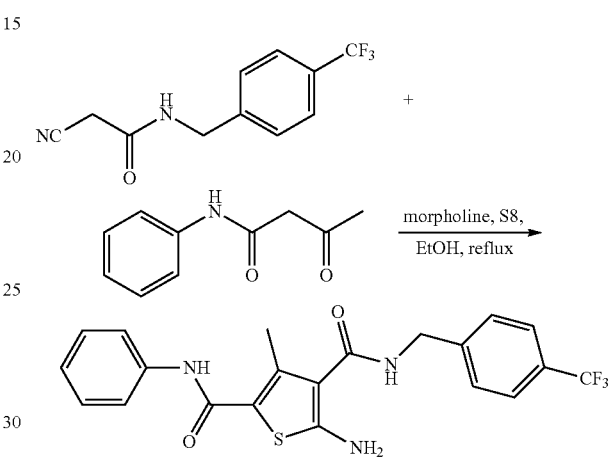

5-Amino-3-methyl-N2-phenyl-N4-(4-(trifluoromethyl)benzyl)thiophene-2,4-dicarboxamide (ZW-790)

To the solution of 2-cyano-N-(4-(trifluoromethyl)benzyl) acetamide (97 mg, 0.40 mmol) in anhydrous EtOH (2 mL), was added acetoacetanilide (71 mg, 0.40 mmol) and sulfur (13 mg, 0.40 mmol), then morpholine (70 mg, 0.80 mmol) was added dropwise to this mixture. The mixture was stirred at 80° C. for 6 hours, TLC shows no start material left, removed the solvent, the residue was purified by flash chromatography on silica gel using hexane:EtOAc (3:2) to obtain desired compounds 121 mg. (73%). 1H NMR: (CD3OD) δ 7.66 (m, 2H), 7.36 (m, 2H), 7.55 (m, 2H), 7.32 (t, J=7.2 Hz, 1H), 7.11 (t, J=7.2 Hz, 2H), 4.61 (s, 2H), 2.53 (s, 3H).

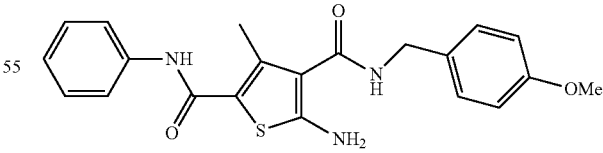

5-Amino-N4-(4-methoxybenzyl)-3-methyl-N2-phenylthiophene-2,4-dicarboxamide (ZW-791)

$^1$H NMR: (CD$_3$OD) δ 7.57 (m, 1H), 7.54 (d, J=7.8 Hz, 1H), 7.46 (m, 4H), 7.23 (m, 2H), 7.02 (m 1H), 4.52 (s, 2H), 2.44 (s, 3H).

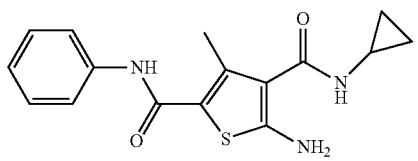 [SMILES: Cc1c(C(=O)Nc2ccccc2)sc(N)c1C(=O)NC1CC1]

5-Amino-N4-cyclopropyl-3-methyl-N2-phenylthiophene-2,4-dicarboxamide (ZW-792)

$^1$H NMR: (CD$_3$OD) δ 7.43 (d, J=7.8 Hz, 2H), 7.23 (t, J=7.8 Hz, 2H), 7.01 (t, J=7.2 Hz, 1H), 2.70 (m, 1H), 2.47 (s, 3H), 0.71 (d, J=6.0 Hz, 2H), 0.51 (m, 2H).

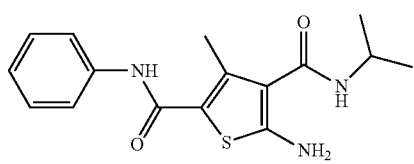 [SMILES: Cc1c(C(=O)Nc2ccccc2)sc(N)c1C(=O)NC(C)C]

5-Amino-3-methyl-N2-phenylthiophene-2,4-dicarboxamide (ZW-793)

$^1$H NMR: (CD$_3$OD) δ 7.52 (d, J=8.4 Hz, 2H), 7.32 (t, J=7.8 Hz, 2H), 7.10 (t, J=7.2 Hz, 1H), 4.14 (m, 1H), 2.45 (s, 3H), 1.23 (s, 3H), 1.22 (s, 3H).

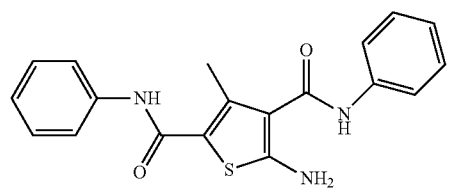 [SMILES: Cc1c(C(=O)Nc2ccccc2)sc(N)c1C(=O)Nc1ccccc1]

5-Amino-3-methyl-N2,N4-diphenylthiophene-2,4-dicarboxamide (ZW-794)

$^1$H NMR: (CD$_3$OD) δ 7.61 (d, J=7.8 Hz, 2H), 7.54 (d, J=7.8 Hz, 2H), 7.34 (m, 4H), 7.11 (m, 2H), 2.45 (s, 3H).

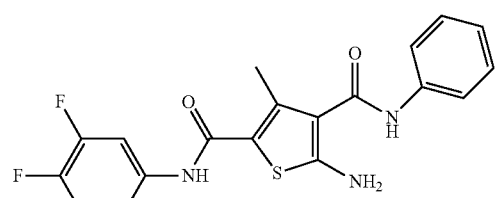

5-Amino-N2-(3,4-difluorophenyl)-3-methyl-N4-phenylthiophene-2,4-dicarboxamide (ZW-892)

$^1$H NMR: (CD$_3$OD) δ 7.56 (m, 1H), 7.51 (d, J=7.8 Hz, 2H), 7.25 (t, J=7.8 Hz, 2H), 7.19 (m, 1H), 7.11 (m, 1H), 7.04 (t, J=7.8 Hz, 1H), 2.49 (s, 3H).

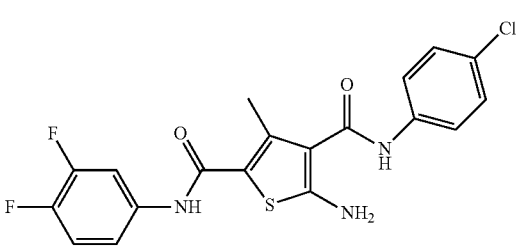 [SMILES: Cc1c(C(=O)Nc2ccc(F)c(F)c2)sc(N)c1C(=O)Nc1ccc(Cl)cc1]

5-Amino-N4-(4-chlorophenyl)-N2-(3,4-difluorophenyl)-3-methylthiophene-2,4-dicarboxamide (ZW-893)

$^1$H NMR: (CD$_3$OD) δ 7.56 (m, 1H), 7.52 (d, J=8.4 Hz, 2H), 7.23 (d, J=8.4 Hz, 2H), 7.18 (m, 1H), 7.10 (m, 1H), 2.49 (s, 3H).

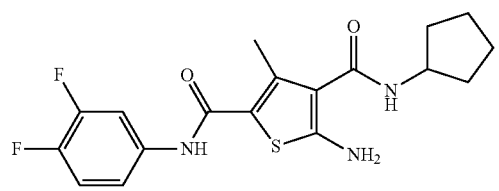 [SMILES: Cc1c(C(=O)Nc2ccc(F)c(F)c2)sc(N)c1C(=O)NC1CCCC1]

5-Amino-N4-cyclopentyl-N2-(3,4-difluorophenyl)-3-methylthiophene-2,4-dicarboxamide (ZW-894)

$^1$H NMR: (CD$_3$OD) δ 7.58 (m, 1H), 7.18 (m, 1H), 7.13 (m, 1H), 4.19 (m, 1H), 2.39 (s, 3H), 1.99 (m, 2H). 1.71 (m, 2H), 1.61 (m, 4H).

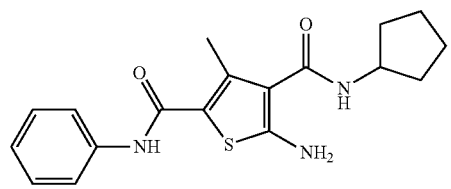 [SMILES: Cc1c(C(=O)Nc2ccccc2)sc(N)c1C(=O)NC1CCCC1]

5-Amino-N4-cyclopentyl-3-methyl-N2-phenylthiophene-2,4-dicarboxamide (ZW-895)

$^1$H NMR: (CD$_3$OD) 7.58 (m, 2H), 7.34 (t, J=8.4 Hz, 1H), 7.26 (t, J=8.4 Hz, 1H), 7.12 (m, 1H), 4 4.19 (m, 1H), 2.39 (s, 3H), 1.93 (m, 2H). 1.67 (m, 2H), 1.56 (m, 2H), 1.50 (m, 2H),

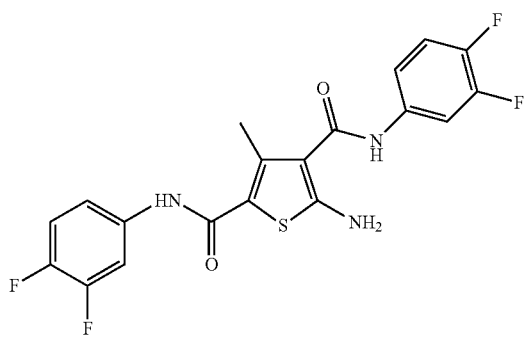 [SMILES: Cc1c(C(=O)Nc2ccc(F)c(F)c2)sc(N)c1C(=O)Nc1ccc(F)c(F)c1]

5-Amino-N2,N4-bis(3,4-difluorophenyl)-3-methyl-thiophene-2,4-dicarboxamide (ZW-932)

¹H NMR: (CD₃OD) δ 7.72 (m, 1H), 7.51 (d, J=7.8 Hz, 2H), 7.61 (m, 1H), 7.25 (m, 1H), 7.17 (m, 2H), 2.49 (s, 3H).

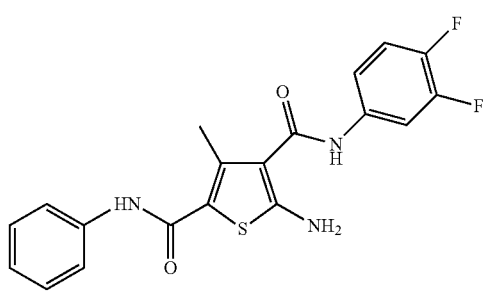 [SMILES: Cc1c(C(=O)Nc2ccccc2)sc(N)c1C(=O)Nc1ccc(F)c(F)c1]

5-Amino-N4-(3,4-difluorophenyl)-3-methyl-N2-phenylthiophene-2,4-dicarboxamide (ZW-933)

¹H NMR: (CD₃OD) δ 7.62 (m, 1H), 7.45 (d, J=7.8 Hz, 2H), 7.24 (t, J=7.8 Hz, 2H), 7.20 (m, 1H), 7.13 (m, 1H), 7.03 (t, J=7.8 Hz, 1H), 2.47 (s, 3H).

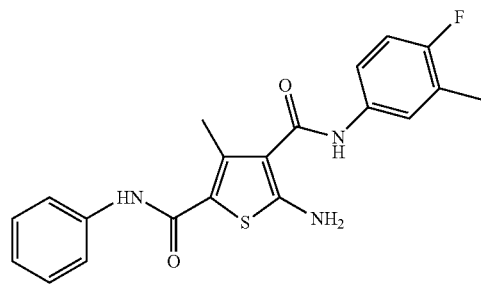 [SMILES: Cc1cc(NC(=O)c2c(N)sc(C(=O)Nc3ccccc3)c2C)ccc1F]

5-Amino-N4-(4-fluoro-3-methylphenyl)-3-methyl-N2-phenylthiophene-2,4-dicarboxamide (ZW-934)

¹H NMR: (CD3OD) δ 7.81 (d, J=8.4 Hz, 2H), 7.74 (d, J=6.6 Hz, 1H), 7.69 (m, 1H), 7.59 (t, J=7.8 Hz, 2H), 7.38 (t, J=7.2 Hz, 1H), 7.27 (t, J=8.4 Hz, 2H), 2.82 (s, 3H), 2.52 (s, 3H).

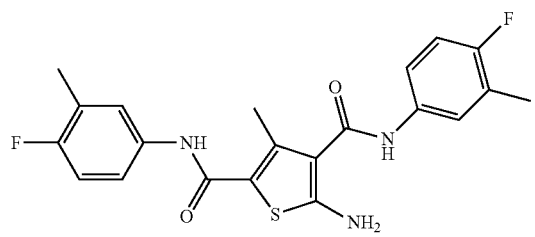 [SMILES: Cc1cc(NC(=O)c2sc(N)c(C(=O)Nc3ccc(F)c(C)c3)c2C)ccc1F]

5-Amino-N2,N4-bis(4-fluoro-3-methylphenyl)-3-methylthiophene-2,4-dicarboxamide (ZW-1070)

¹H NMR: (CD₃OD) δ 7.38 (m, 1H), 7.32 (m, 2H), 7.25 (m, 1H), 6.91 (m, 2H), 2.47 (s, 3H), 2.17 (s, 6H).

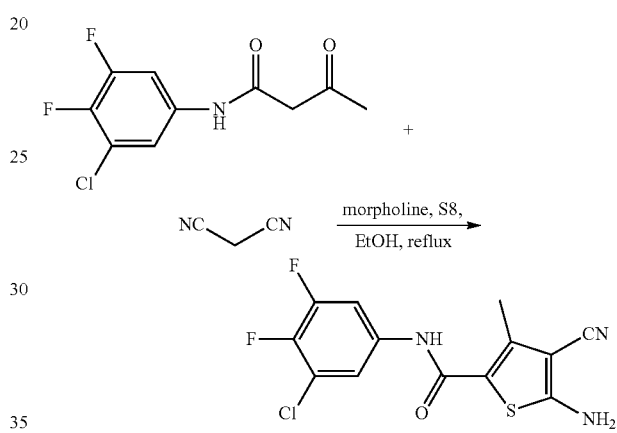

5-Amino-N-(3-chloro-4,5-difluorophenyl)-4-cyano-3-methylthiophene-2-carboxamide (ZW-1042)

To the solution of malononitrile (46 mg, 0.70 mmol) in anhydrous EtOH (3 mL), was added N-(3-chloro-4,5-difluorophenyl)-3-oxobutanamide (173 mg, 0.70 mmol) and sulfur (22 mg, 0.70 mmol), then morpholine (122 mg, 1.40 mmol) was added dropwise to this mixture. The mixture was stirred at 80° C. for 4 hours, TLC shows no start material left, removed the solvent, the residue was purified by flash chromatography on silica gel using hexane: EtOAc (3:2) to obtain desired compounds (56%). ¹H NMR: (CD₃OD) δ 7.36 (s, 1H), 7.34 (s, 1H), 2.35 (s, 3H).

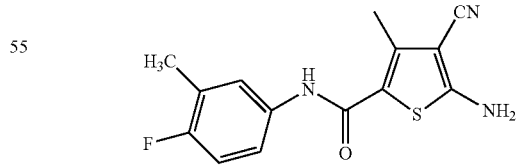

5-Amino-4-cyano-N-(4-fluoro-3-methylphenyl)-3-methylthiophene-2-carboxamide (ZW-1044)

¹H NMR: (CD₃OD) δ 7.67 (d, J=6.6 Hz, 1H), 7.62 (m, 1H), 7.27 (t, J=9.0 Hz, 1H), 2.71 (s, 3H), 2.53 (s, 3H).

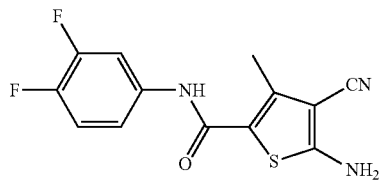 [SMILES: Cc1c(C(=O)Nc2ccc(F)c(F)c2)sc(N)c1C#N]

5-Amino-4-cyano-N-(3,4-difluorophenyl)-3-methyl-thiophene-2-carboxamide (ZW-1043)

$^1$H NMR: (CD$_3$OD) δ 7.64 (dd, J=1.8, 7.2 Hz, 1H), 7.27 (m, 1H), 7.22 (m, 1H), 2.44 (s, 3H).

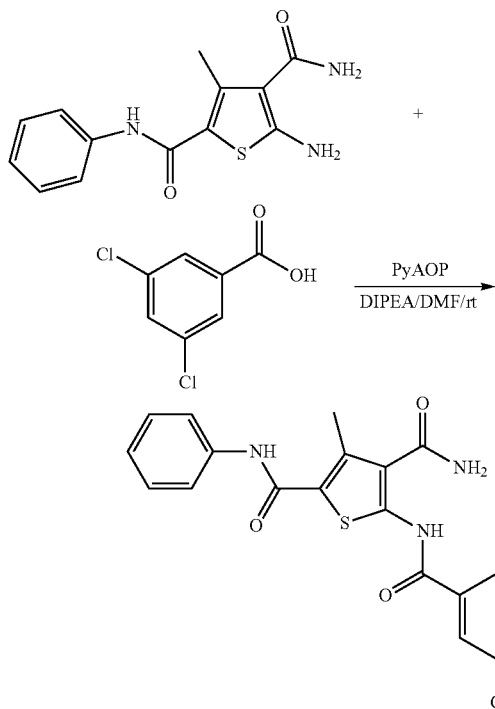

5-(3,5-Dichlorobenzamido)-3-methyl-N2-phenylthiophene-2,4-dicarboxamide (ZW-1040)

To the solution of 3,5-dichlorobenzoic acid (76 mg, 0.40 mmol) in anhydrous DMF (1 mL), was added PyAop (219 mg, 0.42 mmol) and DIEA (139 μl, 0.80 mmol), this reaction mixture was stirred at room temperature for 30 min, then 5-amino-3-methyl-N2-phenylthiophene-2,4-dicarboxamide (110 mg, 0.40 mmol) was added. This reaction mixture was stirred at rt for overnight. Quenched this reaction by adding H$_2$O (5 mL), the aqueous solution was extracted with EtOAc (4×15 mL). The EtOAc portions were combined, washed with brine (2×40 mL), dried over MgSO4, and removed the solvent. The residue was purified by chromatography on silica (gradient elution from hexanes the residue was purified by flash chromatography on silica gel using hexane: EtOAc (3:2) to obtain desired compounds 89 mg (54%). $^1$H NMR: (CD$_3$OD) δ 7.63 (d, J=7.8 Hz, 2H), 7.37 (m, 4H), 7.11 (m, 2H), 2.47 (s, 3H).

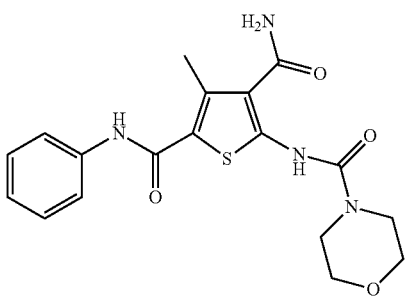 [SMILES: Cc1c(C(=O)Nc2ccccc2)sc(NC(=O)N2CCOCC2)c1C(N)=O]

3-methyl-5-(morpholine-4-carboxamido)-N2-phenylthiophene-2,4-dicarboxamide (ZW-1049)

$^1$H NMR: (DMSO-D$_6$) δ 12.68 (s, 1H), 10.32 (s, 1H), 8.28 (s, 2H), 7.78 (d, J=7.8 Hz, 1H), 7.45 (m, 2H), 7.22 (m, 2H), 3.41 (s, 4H), 2.82 (s, 4H), 2.62 (s, 3H).

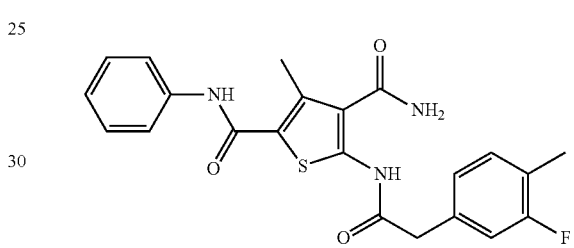

5-(2-(3-Fluoro-4-methylphenyl)acetamido)-3-methyl-N2-phenylthiophene-2,4-dicarboxamide (ZW-1051)

$^1$H NMR: (DMSO-D$_6$) δ 11.36 (s, 1H), 9.94 (s, 1H), 7.64 (d, J=7.8 Hz, 2H), 7.31 (m, 4H), 7.12 (m, 2H), 3.84 (s, 2H), 2.48 (s, 3H), 2.20 (s, 3H).

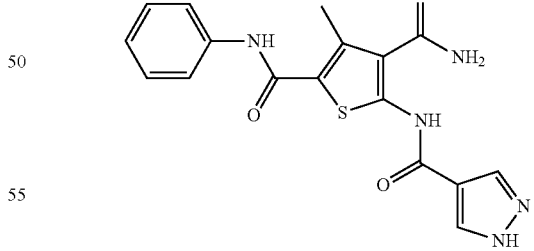

3-Methyl-N2-phenyl-5-(1H-pyrazole-4-carboxamido)thiophene-2,4-dicarboxamide (ZW-1052)

$^1$H NMR: (CD$_3$OD) δ 8.80 (s, 1H), 8.11 (d, J=8.4 Hz, 1H), 7.72 (m, 1H), 7.67 (m, 1H), 7.10 (m, 1H), 6.82 (d, J=7.2 Hz, 2H), 2.42 (s, 3H)

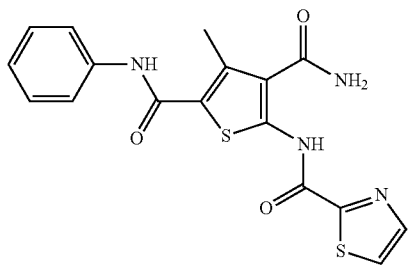 [SMILES: Cc1c(C(=O)Nc2ccccc2)sc(NC(=O)c2nccs2)c1C(N)=O]

3-Methyl-N2-phenyl-5-(thiazole-2-carboxamido)
thiophene-2,4-dicarboxamide (ZW-1053)

$^1$H NMR: (CD$_3$OD) δ 7.99 (m, 1H), 7.81 (m, 1H), 7.63 (t, J=7.8 Hz, 3H), 7.23 (t, J=7.8 Hz, 2H), 2.47 (s, 3H).

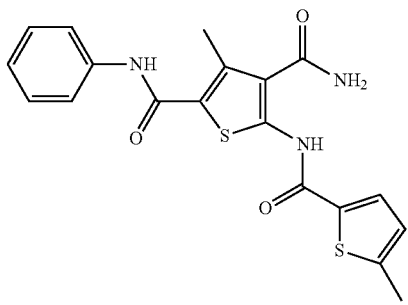

3-Methyl-5-(5-methylthiophene-2-carboxamido)-
N2-phenylthiophene-2,4-dicarboxamide (ZW-1056)

$^1$H NMR: (DMSO-D$_6$) δ 12.68 (s, 1H), 10.32 (s, 1H), 7.67 (d, J=7.8 Hz, 2H), 7.37 (m, 3H), 7.11 (m, 2H), 2.47 (s, 3H), 2.32 (s, 3H).

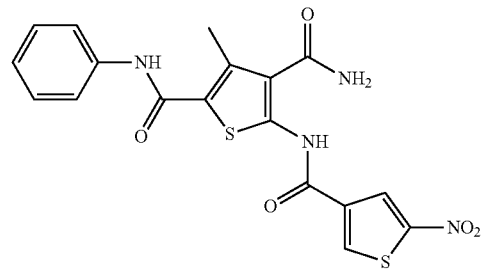 [SMILES: Cc1c(C(=O)Nc2ccccc2)sc(NC(=O)c2csc([N+](=O)[O-])c2)c1C(N)=O]

3-Methyl-5-(5-nitrothiophene-3-carboxamido)-N2-
phenylthiophene-2,4-dicarboxamide (ZW-1054)

$^1$H NMR: (DMSO-D$_6$) δ 12.69 (s, 1H), 10.38 (s, 1H), 8.14 (m, 2H), 8.33 (s, 1H), 7.73 (m, 1H), 7.30 (m, 2H), 7.15 (m, 1H), 7.12 (s, 2H), 2.47 (s, 3H)

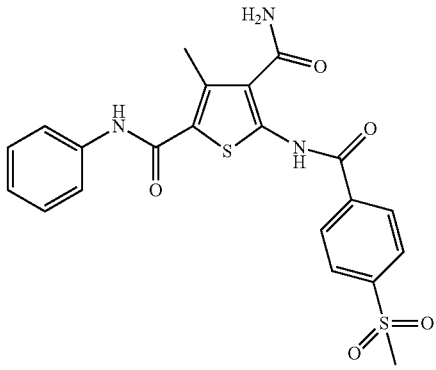

3-Methyl-5-(4-(methylsulfonyl)benzamido)-N2-
phenylthiophene-2,4-dicarboxamide (ZW-1073)

$^1$H NMR: (DMSO-D$_6$) δ 12.82 (s, 1H), 10.20 (s, 1H), 8.24 (m, 2H), 7.76 (d, J=7.8 Hz, 1H), 7.67 (d, J=7.8 Hz, 2H), 7.42 (t, J=7.8 Hz, 1H), 7.37 (m, 3H), 7.18 (t, J=7.8 Hz, 1H), 7.11 (t, J=7.8 Hz, 1H), 4.04 (s, 2H), 2.67 (s, 3H), 2.47 (s, 3H).

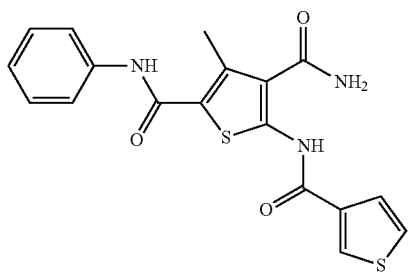 [SMILES: Cc1c(C(=O)Nc2ccccc2)sc(NC(=O)c2ccsc2)c1C(N)=O]

3-Methyl-N2-phenyl-5-(thiophene-3-carboxamido)
thiophene-2,4-dicarboxamide (ZW-1055)

$^1$H NMR: (DMSO-D$_6$) δ 12.67 (s, 1H), 10.30 (s, 1H), 8.24 (m, 2H), 8.46 (s, 1H), 7.67 (d, J=7.8 Hz, 1H), 7.37 (m, 2H), 7.11 (m, 2H), 7.12 (s, 2H), 2.47 (s, 3H).

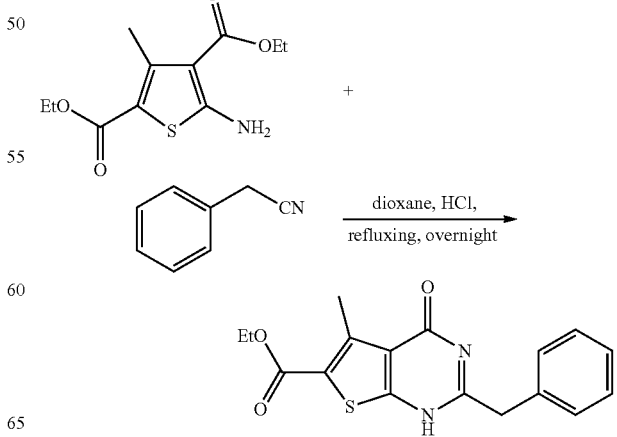

Ethyl 2-benzyl-5-methyl-4-oxo-1,4-dihydrothieno[2,3-d]pyrimidine-6-carboxylate (ZW-772)

Diethyl 5-amino-3-methylthiophene-2,4-dicarboxylate (257 mg, 1.0 mmol), and 2-phenylacetonitrile (117 mg, 1.0 mmol), were placed in 15 mL seal tube at 0° C., the saturated HCl solution in dioxane (2 mL) was added dropwise. The tube was carefully sealed and heated at 100° C. with stirring for 12 h. After it was cooled to rt, the tube was opened carefully due to excessive pressure inside, and the reaction mixture was poured into water (25 mL). The precipitate formed was filtered and washed with a small amount of cold EtOH three times to afford the desired compounds as off-white solid 272 mg. (83%). $^1$H NMR: (DMSO-D$_6$) δ 12.86 (s, 1H), 7.42 (m, 4H), 7.33 (t, J=7.2 Hz, 1H), 4.37 (q, J=7.2 Hz, 2H), 4.02 (s, 2H), 2.87 (s, 3H), 1.37 (t, J=7.2 Hz, 3H).

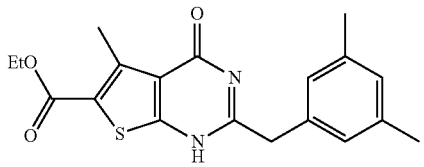 [SMILES: CCOC(=O)c1sc2[nH]c(Cc3cc(C)cc(C)c3)nc(=O)c2c1C]

Ethyl 2-(3,5-dimethylbenzyl)-5-methyl-4-oxo-1,4-dihydrothieno[2,3-d]pyrimidine-6-carboxylate (ZW-773)

$^1$H NMR: (DMSO-D$_6$) δ 12.89 (s, 1H), 7.00 (s, 2H), 6.94 (s, 1H), 4.37 (q, J=7.2 Hz, 2H), 3.93 (s, 2H), 2.87 (s, 6H), 2.47 (s, 3H), 1.37 (t, J=7.2 Hz, 3H).

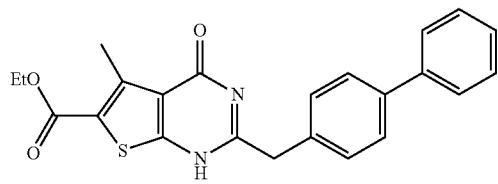 [SMILES: CCOC(=O)c1sc2[nH]c(Cc3ccc(-c4ccccc4)cc3)nc(=O)c2c1C]

Ethyl 2-([1,1'-biphenyl]-4-ylmethyl)-5-methyl-4-oxo-1,4-dihydrothieno[2,3-d]pyrimidine-6-carboxylate (ZW-774)

$^1$H NMR: (DMSO-D6) δ 12.84 (s, 1H), 7.72 (t, J=7.2H, 4H), 7.53 (t, J=7.2H, 4H), 7.43 (t, J=7.2H, 1H), 4.37 (q, J=7.2 Hz, 2H), 4.07 (s, 2H), 2.86 (s, 3H), 1.37 (t, J=7.2 Hz, 3H).

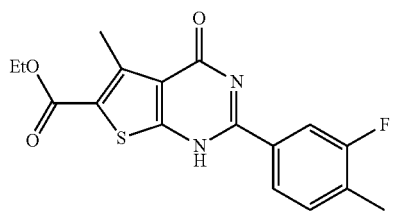 [SMILES: CCOC(=O)c1sc2[nH]c(-c3ccc(C)c(F)c3)nc(=O)c2c1C]

Ethyl 2-(3-fluoro-4-methylphenyl)-5-methyl-4-oxo-1,4-dihydrothieno[2,3-d]pyrimidine-6-carboxylate (ZW-775)

1H NMR: (DMSO-D$_6$) δ 12.84 (s, 1H), 8.03 (m, 2H), 7.53 (t, J=7.8 Hz, 1H), 4.40 (q, J=7.2 Hz, 2H), 2.93 (s, 3H), 2.83 (s, 3H), 1.39 (t, J=7.2 Hz, 3H).

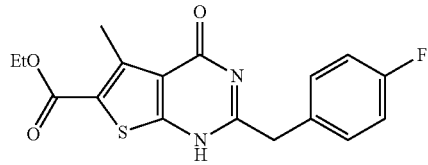 [SMILES: CCOC(=O)c1sc2[nH]c(Cc3ccc(F)cc3)nc(=O)c2c1C]

Ethyl 2-(4-fluorobenzyl)-5-methyl-4-oxo-1,4-dihydrothieno[2,3-d]pyrimidine-6-carboxylate (ZW-776)

1H NMR: (DMSO-D6) δ 12.85 (s, 1H), 7.47 (m, 2H), 7.24 (m, 2H), 4.37 (q, J=7.2 Hz, 2H), 4.02 (s, 2H), 2.86 (s, 3H), 1.39 (t, J=7.2 Hz, 3H).

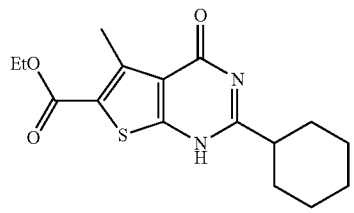 [SMILES: CCOC(=O)c1sc2[nH]c(C3CCCCC3)nc(=O)c2c1C]

Ethyl 2-cyclohexyl-5-methyl-4-oxo-1,4-dihydrothieno[2,3-d]pyrimidine-6-carboxylate (ZW-777)

$^1$H NMR: (DMSO-D$_6$) δ 12.42 (s, 1H), 4.37 (q, J=7.2 Hz, 2H), 2.87 (s, 3H), 2.26 (m, 1H), 1.53 (m, 2H), 1.46 (m, 4H), 1.32 (m, 4H).

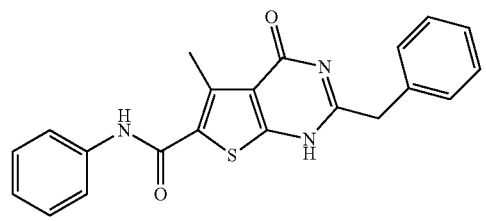 [SMILES: Cc1c(C(=O)Nc2ccccc2)sc2[nH]c(Cc3ccccc3)nc(=O)c12]

2-Benzyl-5-methyl-4-oxo-N-phenyl-1,4-dihydrothieno[2,3-d]pyrimidine-6-carboxamide (ZW-937)

$^1$H NMR: (DMSO-D$_6$) δ 12.81 (s, 1H), 10.22 (s, 1H), 7.73 (d, J=7.8 Hz, 2H), 7.41 (m, 6H), 7.33 (m, 1H), 7.19 (t, J=7.2 Hz, 1H), 4.04 (s, 2H), 2.77 (s, 3H).

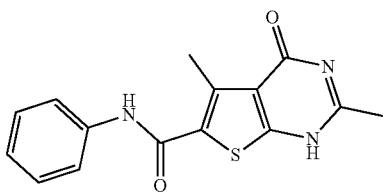 [SMILES: Cc1nc(=O)c2c(C)c(C(=O)Nc3ccccc3)sc2[nH]1]

2,5-Dimethyl-4-oxo-N-phenyl-1,4-dihydrothieno[2,3-d]pyrimidine-6-carboxamide (ZW-936)

$^1$H NMR: (DMSO-D$_6$) δ 12.56 (s, 1H), 10.25 (s, 1H), 7.45 (d, J=7.2 Hz, 2H), 7.43 (t, J=7.2 Hz, 2H), 7.19 (t, J=7.2 Hz, 1H), 2.78 (s, 3H), 2.44 (s, 3H).

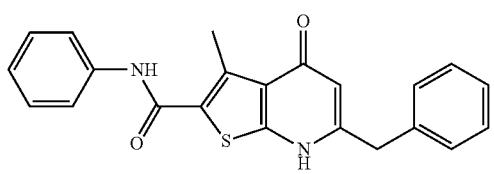 [SMILES: Cc1c(C(=O)Nc2ccccc2)sc2[nH]c(Cc3ccccc3)cc(=O)c12]

2-Benzyl-5-methyl-4-oxo-N-phenyl-1,4-dihydrothieno[2,3-d]pyrimidine-6-carboxamide (ZW-937)

$^1$H NMR: (DMSO-D$_6$) δ 12.79 (s, 1H), 10.22 (s, 1H), 7.72 (d, J=7.8 Hz, 2H), 7.42 (m, 4H), 7.33 (t, J=7.2 Hz, 2H), 7.19 (t, J=7.2 Hz, 2H), 4.03 (s, 2H), 2.77 (s, 3H).

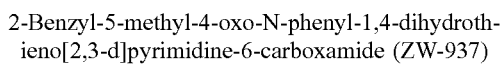

2-(3,4-Difluorophenyl)-5-methyl-4-oxo-N-phenyl-1,4-dihydrothieno[2,3-d]pyrimidine-6-carboxamide (ZW-938)

$^1$H NMR: (DMSO-D$_6$) δ 12.82 (s, 1H), 10.33 (s, 1H), 8.34 (m, 1H), 8.15 (m, 2H), 7.76 (m, 2H), 7.45 (t, J=7.8 Hz, 2H), 7.21 (t, J=7.8 Hz, 1H), 2.84 (s, 3H).

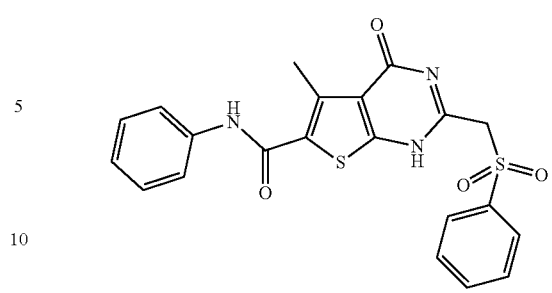

5-Methyl-4-oxo-N-phenyl-2-((phenylsulfonyl)methyl)-1,4-dihydrothieno[2,3-d]pyrimidine-6-carboxamide (ZW-939)

$^1$H NMR: (CD$_3$OD) δ 7.76 (m, 3H), 7.66 (t, J=7.2 Hz, 1H), 7.53 (m, 3H), 7.28 (t, J=7.2 Hz, 2H), 7.08 (t, J=7.2 Hz, 1H), 4.48 (s, 2H), 2.70 (s, 3H).

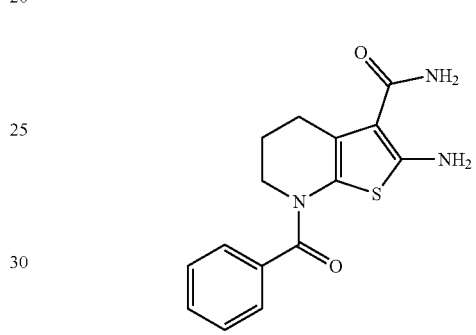

2-Amino-7-benzoyl-4,5,6,7-tetrahydrothieno [2,3-b]pyridine-3-carboxamide (ZW-1071)

$^1$H NMR: (DMSO-D$_6$) δ 7.55 (m, 5H), 6.82 (s, 2H), 6.67 (s, 2H), 3.70 (m 2H), 2.81 (t, J=6.6 Hz, 2H), 1.95 (m, 2H).

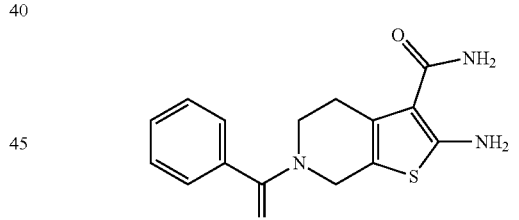

2-Amino-6-benzoyl-4,5,6,7-tetrahydrothieno [2,3-c]pyridine-3-carboxamide (ZW-1072)

$^1$H NMR: (DMSO-D$_6$) δ 7.56 (m, 5H), 7.06 (s, 2H), 6.68 (s, 2H), 4.60 (s 2H), 3.54 (t, J=6.6 Hz, 2H), 2.82 (m, 2H).

TABLE 2

| Compd # | Compd ID | Structure | TSA | EC$_{50}$ (μM) | CC$_{50}$ (μM) | SI |
|---|---|---|---|---|---|---|
| 1 | HF9C6 | 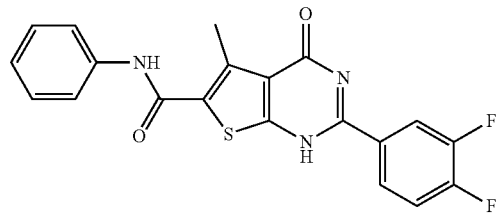 [SMILES: Cc1c(C(=O)Nc2ccccc2)sc2[nH]c(-c3ccc(F)c(F)c3)nc(=O)c12] | +++ | 34 ± 0.6 | >100 | >29 |

TABLE 2-continued

| Compd # | Compd ID | Structure | TSA | EC$_{50}$ (μM) | CC$_{50}$ (μM) | SI |
|---|---|---|---|---|---|---|
| 2 | ZW-769 | 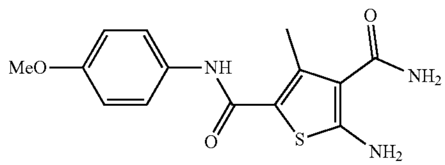 | +++ | ~10 | ND | |
| 3 | ZW-770 | 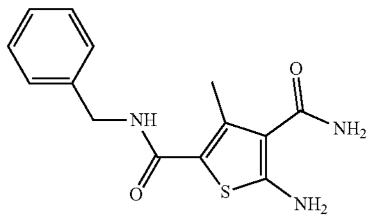 [SMILES: Cc1c(C(=O)NCc2ccccc2)sc(N)c1C(N)=O] | +++ | ~10 | ND | |
| 4 | ZW-771 | 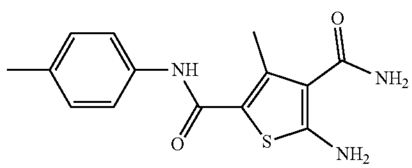 [SMILES: Cc1ccc(NC(=O)c2sc(N)c(C(N)=O)c2C)cc1] | − | >10 | ND | |
| 5 | ZW-772 | 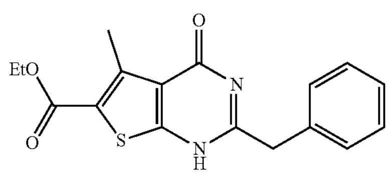 [SMILES: CCOC(=O)c1sc2[nH]c(Cc3ccccc3)nc(=O)c2c1C] | − | >10 | ND | |
| 6 | ZW-773 | 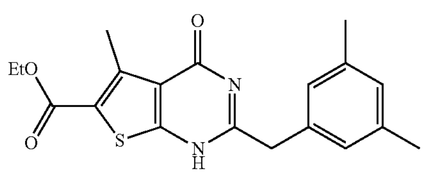 [SMILES: CCOC(=O)c1sc2[nH]c(Cc3cc(C)cc(C)c3)nc(=O)c2c1C] | − | >10 | ND | |
| 7 | ZW-774 | 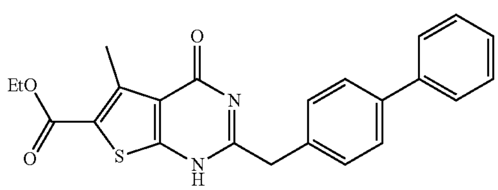 [SMILES: CCOC(=O)c1sc2[nH]c(Cc3ccc(-c4ccccc4)cc3)nc(=O)c2c1C] | − | >10 | ND | |
| 8 | ZW-775 | 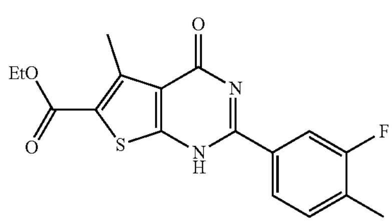 [SMILES: CCOC(=O)c1sc2[nH]c(-c3ccc(C)c(F)c3)nc(=O)c2c1C] | − | >10 | ND | |
| 9 | ZW-776 | 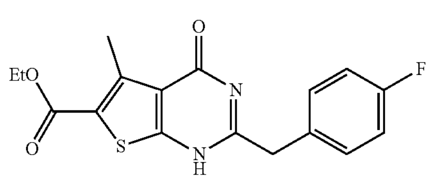 [SMILES: CCOC(=O)c1sc2[nH]c(Cc3ccc(F)cc3)nc(=O)c2c1C] | − | >10 | ND | |

TABLE 2-continued
| Compd # | Compd ID | Structure | TSA | EC$_{50}$ (μM) | CC$_{50}$ (μM) | SI |
|---|---|---|---|---|---|---|
| 10 | ZW-777 | 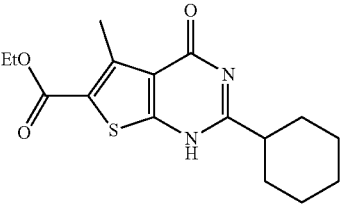 | – | >10 | ND | |
| 11 | ZW-790 | 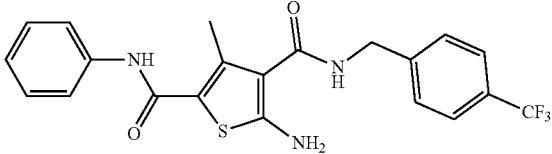 [SMILES: Cc1c(C(=O)Nc2ccccc2)sc(N)c1C(=O)NCc1ccc(C(F)(F)F)cc1] | +++ | >10 | ND | |
| 12 | ZW-791 | 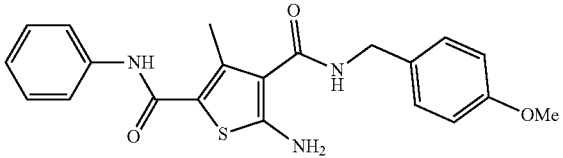 [SMILES: COc1ccc(CNC(=O)c2c(N)sc(C(=O)Nc3ccccc3)c2C)cc1] | +++ | >10 | ND | |
| 13 | ZW-792 | 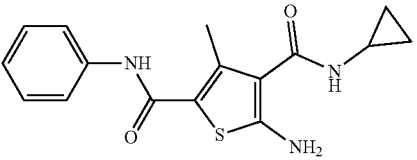 [SMILES: Cc1c(C(=O)Nc2ccccc2)sc(N)c1C(=O)NC1CC1] | – | >10 | ND | |
| 14 | ZW-793 | 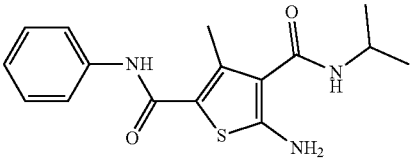 | – | >10 | ND | |
| 15 | ZW-794 | 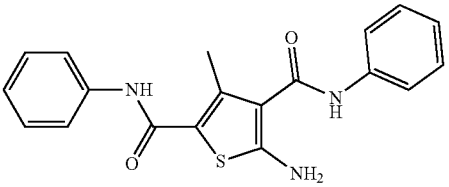 [SMILES: Cc1c(C(=O)Nc2ccccc2)sc(N)c1C(=O)Nc1ccccc1] | +++ | 3.2 ± 0.3 | >100 | >31 |
| 16 | ZW-892 | 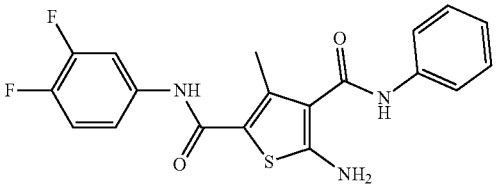 [SMILES: Cc1c(C(=O)Nc2ccc(F)c(F)c2)sc(N)c1C(=O)Nc1ccccc1] | +++ | 3.4 ± 0.3 | 26.2 ± 2.7 | 8 |
| 17 | ZW-893 | 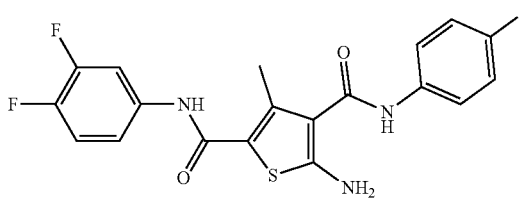 | +++ | >10 | ND | |

TABLE 2-continued

| Compd # | Compd ID | Structure | TSA | EC$_{50}$ (μM) | CC$_{50}$ (μM) | SI |
|---|---|---|---|---|---|---|
| 18 | ZW-894 | 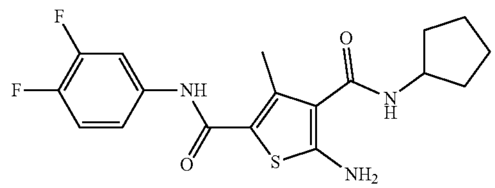 | +++ | >10 | ND | |
| 19 | ZW-895 | 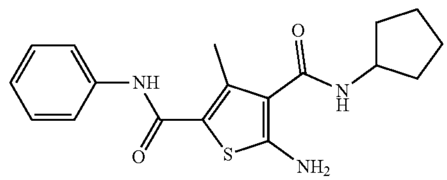 [SMILES: Cc1c(C(=O)Nc2ccccc2)sc(N)c1C(=O)NC1CCCC1] | − | >10 | ND | |
| 20 | ZW-896 | 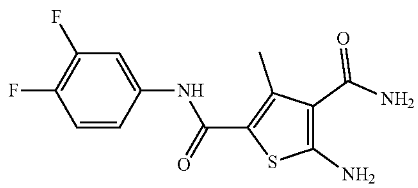 [SMILES: Cc1c(C(=O)Nc2ccc(F)c(F)c2)sc(N)c1C(N)=O] | +++ | 0.76 ± 0.22 | >100 | >132 |
| 21 | ZW-932 | 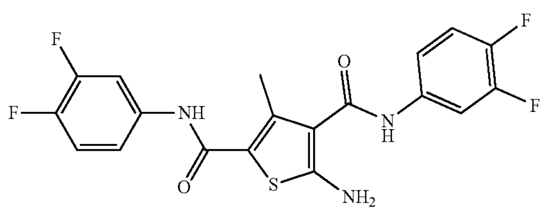 [SMILES: Cc1c(C(=O)Nc2ccc(F)c(F)c2)sc(N)c1C(=O)Nc1ccc(F)c(F)c1] | ++ | 3.6 ± 1.6 | 17.4 ± 1.3 | 5 |
| 22 | ZW-933 | 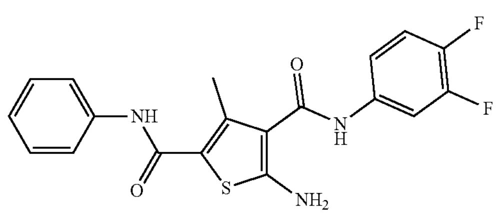 [SMILES: Cc1c(C(=O)Nc2ccccc2)sc(N)c1C(=O)Nc1ccc(F)c(F)c1] | +++ | 2.4 ± 0.2 | 40.5 ± 5.1 | 17 |
| 23 | ZW-934 | 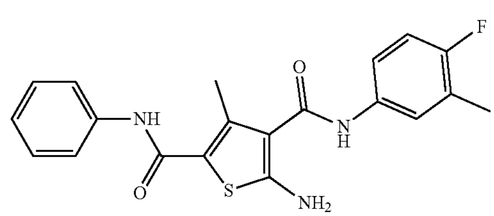 [SMILES: Cc1cc(NC(=O)c2c(N)sc(C(=O)Nc3ccccc3)c2C)ccc1F] | +++ | 0.68 ± 0.01 | 39.6 ± 2.6 | 58 |
| 24 | ZW-935 | 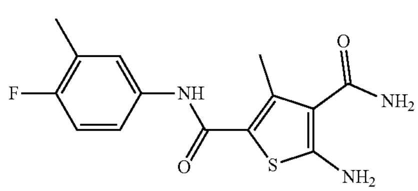 [SMILES: Cc1cc(NC(=O)c2sc(N)c(C(N)=O)c2C)ccc1F] | +++ | 0.21 ± 0.09 | >100 | >476 |
| 25 | ZW-936 | 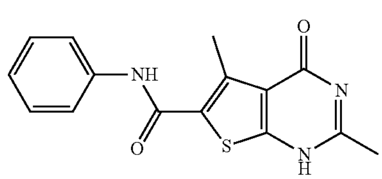 [SMILES: Cc1nc(=O)c2c(C)c(C(=O)Nc3ccccc3)sc2[nH]1] | − | ND | ND | |

TABLE 2-continued
| Compd # | Compd ID | Structure | TSA | EC$_{50}$ (μM) | CC$_{50}$ (μM) | SI |
|---|---|---|---|---|---|---|
| 26 | ZW-937 | 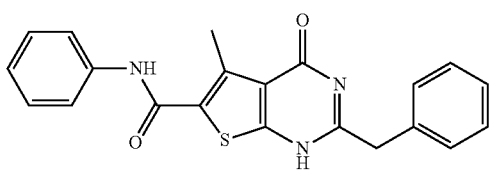 [SMILES: Cc1c(C(=O)Nc2ccccc2)sc2[nH]c(Cc3ccccc3)nc(=O)c12] | − | ND | ND | |
| 27 | ZW-938 | 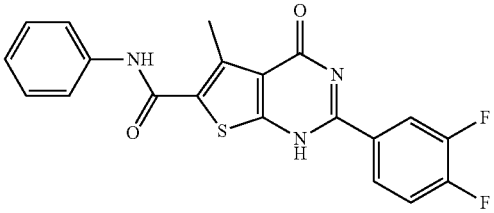 [SMILES: Cc1c(C(=O)Nc2ccccc2)sc2[nH]c(-c3ccc(F)c(F)c3)nc(=O)c12] | − | ND | ND | |
| 28 | ZW-939 | 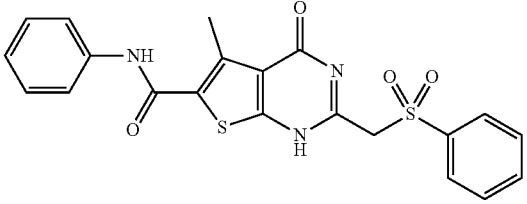 [SMILES: Cc1c(C(=O)Nc2ccccc2)sc2[nH]c(CS(=O)(=O)c3ccccc3)nc(=O)c12] | − | ND | ND | |
| 29 | ZW-1034 | 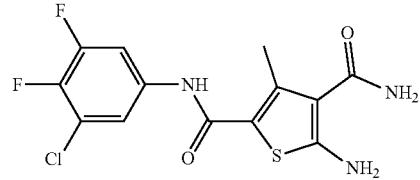 [SMILES: Cc1c(C(=O)Nc2cc(F)c(F)c(Cl)c2)sc(N)c1C(N)=O] | +++ | 4.6 ± 1.1 | 71.8 ± 4.1 | 16 |
| 30 | ZW-1035 | 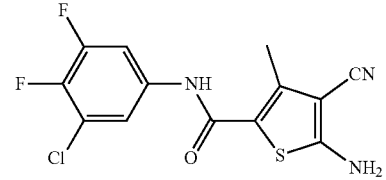 | − | ND | ND | |
| 31 | ZW-1036 | 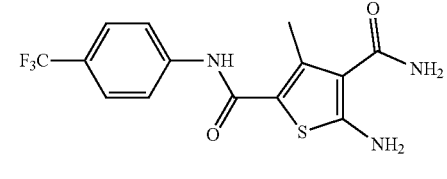 [SMILES: Cc1c(C(=O)Nc2ccc(C(F)(F)F)cc2)sc(N)c1C(N)=O] | − | ND | ND | |
| 32 | ZW-1037 | 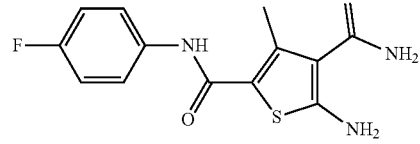 | +++ | 3.0 ± 0.7 | >100 | >33 |
| 33 | ZW-1038 | 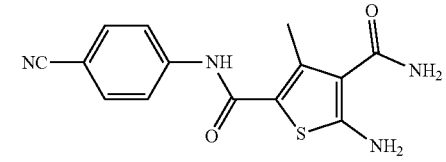 [SMILES: Cc1c(C(=O)Nc2ccc(C#N)cc2)sc(N)c1C(N)=O] | − | ND | ND | |

TABLE 2-continued

| Compd # | Compd ID | Structure | TSA | EC$_{50}$ (μM) | CC$_{50}$ (μM) | SI |
|---|---|---|---|---|---|---|
| 34 | ZW-1039 | 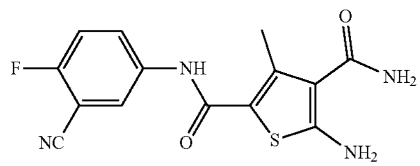 [SMILES: Cc1c(C(=O)Nc2ccc(F)c(C#N)c2)sc(N)c1C(N)=O] | +++ | 0.47 ± 0.25 | >100 | >213 |
| 35 | ZW-1040 | 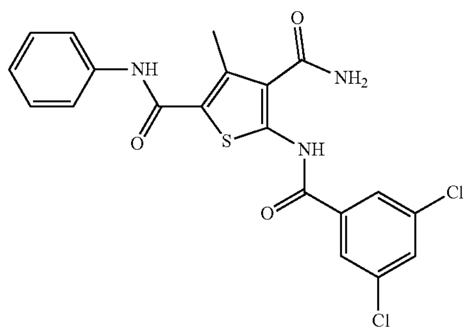 [SMILES: Cc1c(C(=O)Nc2ccccc2)sc(NC(=O)c2cc(Cl)cc(Cl)c2)c1C(N)=O] | +++ | 2.7 ± 1.9 | 49.5 ± 0.1 | >37 |
| 36 | ZW-1041 | 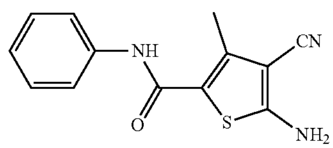 [SMILES: Cc1c(C(=O)Nc2ccccc2)sc(N)c1C#N] | − | ND | ND | |
| 37 | ZW-1042 | 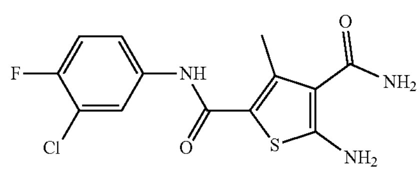 [SMILES: Cc1c(C(=O)Nc2ccc(F)c(Cl)c2)sc(N)c1C(N)=O] | +++ | 0.31 ± 0.07 | >100 | >323 |
| 38 | ZW-1043 | 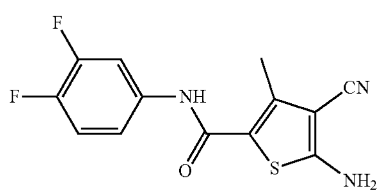 [SMILES: Cc1c(C(=O)Nc2ccc(F)c(F)c2)sc(N)c1C#N] | +++ | ~10 | >100 | |
| 39 | ZW-1044 | 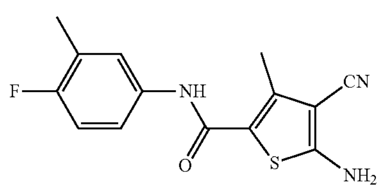 [SMILES: Cc1cc(NC(=O)c2sc(N)c(C#N)c2C)ccc1F] | +++ | 2.0 ± 0.2 | 96.1 ± 10.1 | 48 |
| 40 | ZW-1045 | 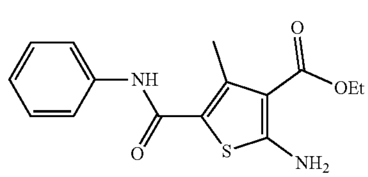 [SMILES: CCOC(=O)c1c(N)sc(C(=O)Nc2ccccc2)c1C] | +++ | >10 | 75.9 ± 1.8 | <8 |
| 41 | ZW-1046 | 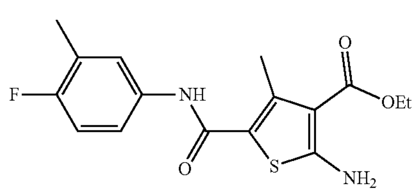 [SMILES: CCOC(=O)c1c(N)sc(C(=O)Nc2ccc(F)c(C)c2)c1C] | +++ | 6.1 ± 2.8 | >100 | >16 |

TABLE 2-continued

| Compd # | Compd ID | Structure | TSA | EC$_{50}$ (µM) | CC$_{50}$ (µM) | SI |
|---|---|---|---|---|---|---|
| 42 | ZW-1047 | 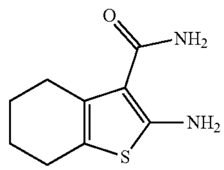 [SMILES: NC(=O)c1c(N)sc2c1CCCC2] | − | ND | ND | |
| 43 | ZW-1048 | 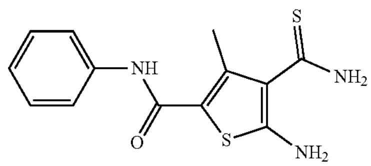 [SMILES: Cc1c(C(=O)Nc2ccccc2)sc(N)c1C(N)=S] | +++ | >10 | >100 | |
| 44 | ZW-1049 | 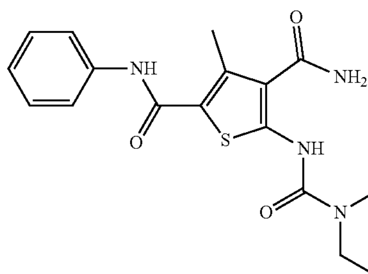 | − | ND | ND | |
| 45 | ZW-1050 | 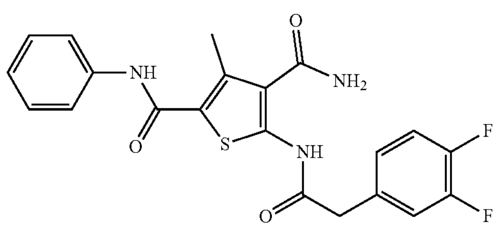 [SMILES: Cc1c(C(=O)Nc2ccccc2)sc(NC(=O)Cc2ccc(F)c(F)c2)c1C(N)=O] | + | ~10 | >100 | |
| 46 | ZW-1051 | 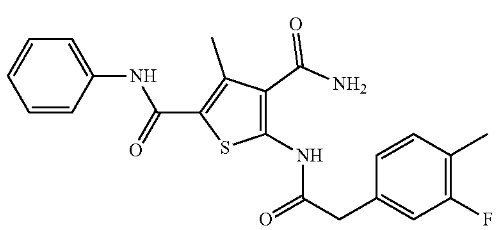 [SMILES: Cc1ccc(CC(=O)Nc2sc(C(=O)Nc3ccccc3)c(C)c2C(N)=O)cc1F] | + | >10 | >100 | |
| 47 | ZW-1052 | 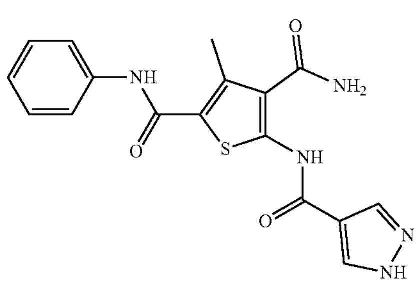 [SMILES: Cc1c(C(=O)Nc2ccccc2)sc(NC(=O)c2cn[nH]c2)c1C(N)=O] | +++ | 4.7 ± 0.4 | >100 | >21 |

TABLE 2-continued

| Compd # | Compd ID | Structure | TSA | EC$_{50}$ (µM) | CC$_{50}$ (µM) | SI |
|---|---|---|---|---|---|---|
| 48 | ZW-1053 | 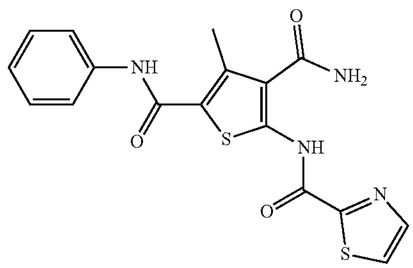 [SMILES: Cc1c(C(=O)Nc2ccccc2)sc(NC(=O)c2nccs2)c1C(N)=O] | +++ | 4.1 ± 2.2 | >100 | >24 |
| 49 | ZW-1054 | 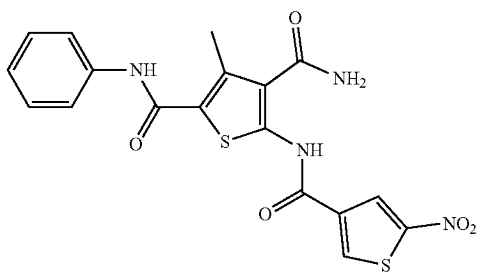 [SMILES: Cc1c(C(=O)Nc2ccccc2)sc(NC(=O)c2csc([N+](=O)[O-])c2)c1C(N)=O] | + | 2.9 ± 0.7 | >100 | >34 |
| 50 | ZW-1055 | 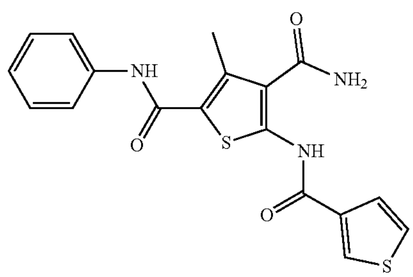 [SMILES: Cc1c(C(=O)Nc2ccccc2)sc(NC(=O)c2ccsc2)c1C(N)=O] | +++ | 2.1 ± 0.3 | >100 | >48 |
| 51 | ZW-1056 | 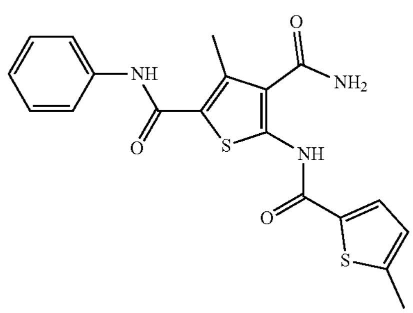 [SMILES: Cc1ccc(C(=O)Nc2sc(C(=O)Nc3ccccc3)c(C)c2C(N)=O)s1] | +++ | 3.5 ± 2.1 | >100 | >29 |
| 52 | ZW-1057 | 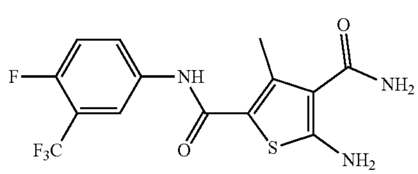 [SMILES: Cc1c(C(=O)Nc2ccc(F)c(C(F)(F)F)c2)sc(N)c1C(N)=O] | +++ | 1.2 ± 0.03 | >100 | >83 |
| 53 | ZW-1066 | 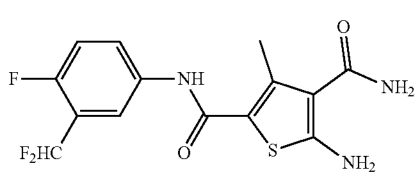 | +++ | 0.11 ± 0.01 | >100 | >909 |

TABLE 2-continued

| Compd # | Compd ID | Structure | TSA | EC$_{50}$ (μM) | CC$_{50}$ (μM) | SI |
|---|---|---|---|---|---|---|
| 54 | ZW-1067 | 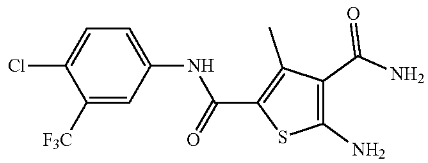 | +++ | 4.6 ± 0.4 | 72.1 ± 6.4 | 16 |
| 55 | ZW-1068 | 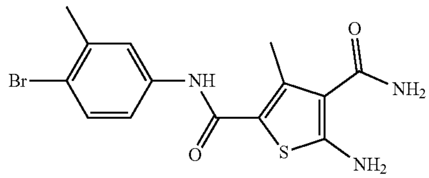 [SMILES: Cc1cc(NC(=O)c2sc(N)c(C(N)=O)c2C)ccc1Cl] | +++ | 7.1 ± 1.7 | 107.2 ± 7.2 | 15 |
| 56 | ZW-1069 | 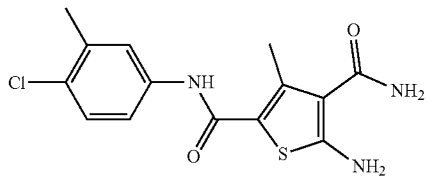 | +++ | 1.7 ± 0.4 | >100 | >59 |
| 57 | ZW-1070 | 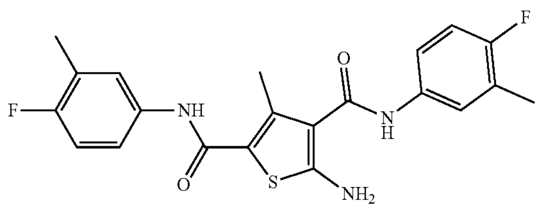 | − | ND | ND | |
| 58 | ZW-1071 | 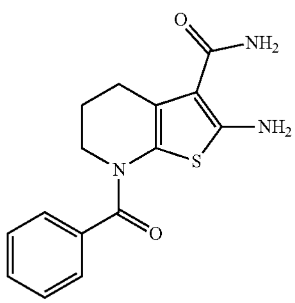 [SMILES: NC(=O)c1c(N)sc2c1CCCN2C(=O)c1ccccc1] | − | ND | ND | |
| 59 | ZW-1072 | 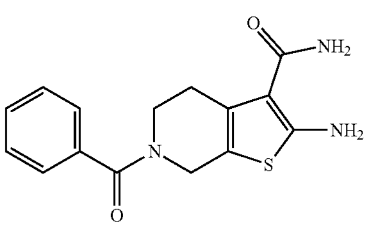 [SMILES: NC(=O)c1c(N)sc2c1CCN(C(=O)c1ccccc1)C2] | − | ND | ND | |
| 60 | ZW-1073 | 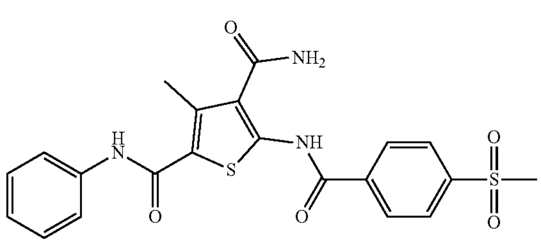 [SMILES: Cc1c(C(=O)Nc2ccccc2)sc(NC(=O)c2ccc(S(C)(=O)=O)cc2)c1C(N)=O] | +++ | 1.4 ± 0.02 | >100 | >71 |

TABLE 2-continued

| Compd # | Compd ID | Structure | TSA | EC$_{50}$ (μM) | CC$_{50}$ (μM) | SI |
|---|---|---|---|---|---|---|
| 61 | ZW-1074 | 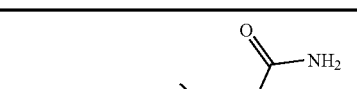 | — | ND | ND |  |

After testing several compounds, it was observed that analogs showing no effect in TSA did not inhibit HBV replication; therefore, compounds with no apparent effect on Cp melting were not tested in cell-based assays. The presently disclosed medicinal chemistry efforts yielded potent analogs with EC$_{50}$ values as low as 110 nM.

Example 16—HF9C6 and Analogs Bind Cp Similarly to SBAs

The binding site for HAPs and SBAs has been found using X-ray crystallography and mutagenesis techniques. The interactions within the pocket, however, are markedly different between these 2 classes. To probe this binding site, HBV-expressing plasmids with mutations in Cp (Y118F, T109S, T109M, T109I, I105V, I105L, and I105T) were generated (Klumpp, et al., *Proc. Natl. Acad. Sci. USA* 112:15196-15201, 2015). Huh7 cells were transfected with either wild-type (WT) or mutant plasmid, treated with Bay 38-7690 (500 nM), DVR-56 (250 nM), ZW-935 (250 nM), or HF9C6 (4 μM), and assessed for HBV core-associated DNA by qPCR. The compound concentrations used were sufficient to suppress viral DNA production by 75%; therefore, mutant resistance and hypersusceptibility could be easily observed at a single dose.

Figure 4A:
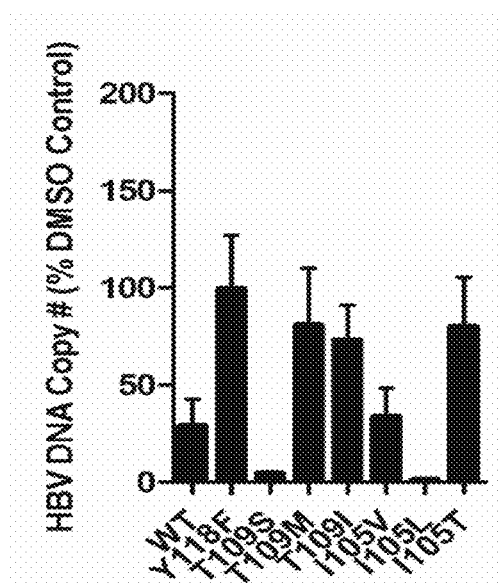
FIG. 4A-FIG. 4D. HF9C6 and analogs bind Cp similarly to SBAs, and have distinct resistance profiles from Bay 38-7690. Huh7 cells were transfected with HBV-expressing plasmids harboring the indicated mutations in Cp, treated with 500 nM Bay 38-7690 (FIG. 4A), 250 nM DVR-56 (FIG. 4B), 4 µM HF9C6 (FIG. 4C), or 250 nM ZW-935 (FIG. 4D), and assessed for HBV core-associated DNA by qPCR.
Figure 4B:
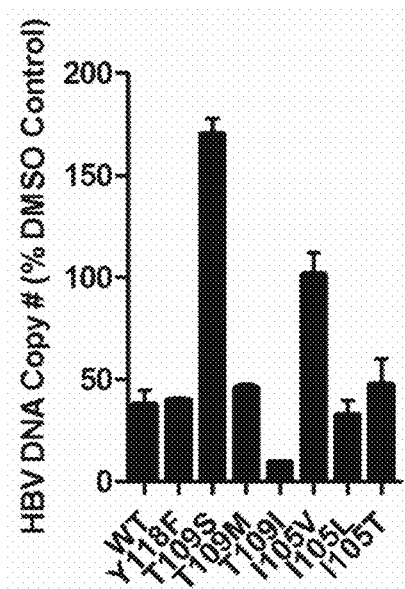
Figure 4C:
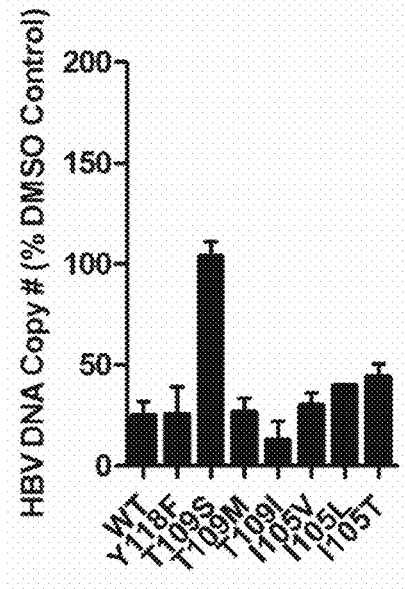
Figure 4D:
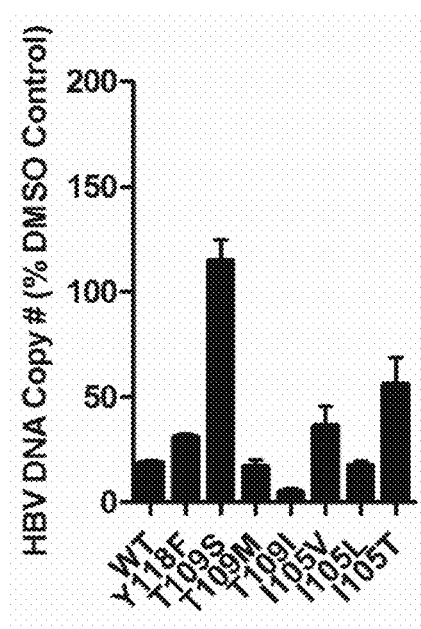

As shown in FIG. 4A, Bay 38-7690 (a HAP) has the same resistance profile as previously reported (Klumpp, et al., supra, 2015); specifically, the Y118F, T109M, T109I, and I105T mutants are resistant to Bay, while T109S and I105L are hypersusceptible. The resistance profile for SBAs for these specific mutants has not been tested, but it has been shown that SBAs interact differently with Cp than do HAPs with the use of different mutants (Zhou, et al., supra, 2017). The present experiment showed that the T109S and I105V mutants are resistant to the SBA DVR-56, while T109I is hypersusceptible (FIG. 4B). When tested against the pool of mutants, the present experiment showed that the resistance profiles of HF9C6 and ZW-935 are highly similar to that of DVR-56 (FIG. 4C, FIG. 4D). Specifically, while I105V does not impart significant resistance as it does to DVR-56, the T109S and T109I mutants confer resistance and hypersusceptibility, respectively, to HF9C6 and ZW-935. These data suggest that HF9C6 and analogs bind Cp in a similar manner to SBAs. Furthermore, this suggests that although HAPs, SBAs, and HF9C6 analogs share the same target, HF9C6 analogs can be suitable in combination therapies with HAPs and SBAs to more effectively treat HBV infections and overcome escape mutants.

While the invention has been described in connection with specific embodiments thereof, it will be understood that the inventive methodology is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth and as follows in scope of the appended claims.

The invention claimed is:

1. A composition comprising a compound of formula:

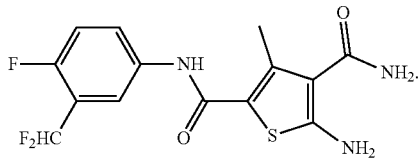 [SMILES: Cc1c(C(=O)Nc2ccc(F)c(C(F)F)c2)sc(N)c1C(N)=O]

2. The composition of claim 1, further comprising a pharmaceutically acceptable excipient.

3. A method of inhibiting the replication of a hepatitis B virus (HBV) comprising contacting said HBV with at least a first composition comprising a compound of formula:

4. The method of claim 3, wherein said HBV is present inside of a cell, and said contacting comprises contacting said cell with said composition.

5. The method of claim 3, wherein said composition further comprises an additional antiviral compound.

6. The method of claim 5, wherein said additional antiviral compound is a heteroaryldyhydropyrimidine (HAP) or a sulfamoylbenzamide (SBA).

* * * * *